United States Patent [19]
Green et al.

[11] Patent Number: 5,601,831
[45] Date of Patent: Feb. 11, 1997

[54] **VACCINES FOR NONTYPABLE *HAEMOPHILUS INFLUENZAE***

[75] Inventors: Bruce A. Green, Pittsford; Gary W. Zlotnick, Penfield, both of N.Y.

[73] Assignee: Praxis Biologics, Inc., Rochester, N.Y.

[21] Appl. No.: 491,466

[22] Filed: Mar. 9, 1990

Related U.S. Application Data

[63] Continuation-in-part of Ser. No. 320,971, Mar. 9, 1989, abandoned.

[51] Int. Cl.$^6$ .................. A61K 39/102; A61K 39/385
[52] U.S. Cl. .................. 424/256.1; 424/282.1; 424/193.1; 424/192.1; 424/185.1
[58] Field of Search .................. 424/89, 92, 93, 424/256.1, 282.1, 193.1, 192.1, 185.1

[56] References Cited

U.S. PATENT DOCUMENTS

| | | | |
|---|---|---|---|
| 4,220,717 | 9/1980 | Kuo | 424/184.1 |
| 4,356,170 | 10/1982 | Jennings | 424/184.1 |
| 4,707,543 | 11/1987 | Zollinger et al. | 530/402 |
| 4,762,713 | 8/1988 | Anderson | 424/184.1 |
| 4,830,852 | 5/1989 | Marburg | 424/130.1 |
| 4,873,090 | 10/1989 | Clancy | 424/184.1 |

FOREIGN PATENT DOCUMENTS

| | | |
|---|---|---|
| 0098581 | 1/1984 | European Pat. Off. . |
| 0281673 | 9/1988 | European Pat. Off. . |
| 0320289 | 6/1989 | European Pat. Off. . |
| WO88/04932 | 7/1988 | WIPO . |

OTHER PUBLICATIONS

Schneerson et al. Journal of Exp. Med. 361 vol. 152 1980.
Deitch et al. Journal of Bacteriology vol. 170 No. 2 Feb. 1988 pp. 489–498.
Munson, R. S. and D. M. Granoff, *Infect. Immun.* 49:544–549 (1985).
Granoff, D. M. and R. S. Munson, *J. Infect. Diseases* 153:448–461 (1986).
Honberg, P. Z., *Acta Path. Microbiol. Immunol. Scand.Sect. B* 93:175–179 (1985).
van Alphen, L. et al., *J. Bacteriol.* 155:878–885 (1983).

*Primary Examiner*—Lila Feisee
*Attorney, Agent, or Firm*—Alan M. Gordon

[57] ABSTRACT

Protein "e" of *H. influenzae*, a lipoprotein of approximately 28,000 daltons, has been purified and sequenced. Protein "e" and peptides or proteins having a shared epitope, can be used to vaccinate against non-typable (and typable) *H. influenzae* and to prevent otitis media caused by *H. influenzae*. For this purpose, protein "e" or derivatives thereof can be produced in native, synthetic or recombinant forms and can be administered alone or in conjunction with other antigens of *H. influenzae*. Protein "e" can also be used in multivalent vaccines designed for *H. influenzae* and one or more other infectious organisms.

33 Claims, 9 Drawing Sheets

FIG.2a  Mab EPR-5.2.1
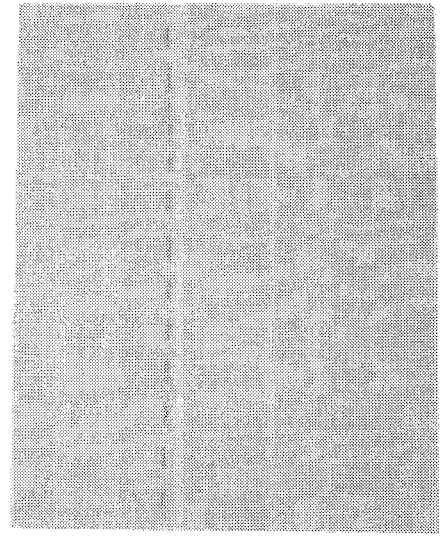
1 2 3 4 5 6 7 8 9 10 11 12
FIG.2b  Mab EPR-17.2.1
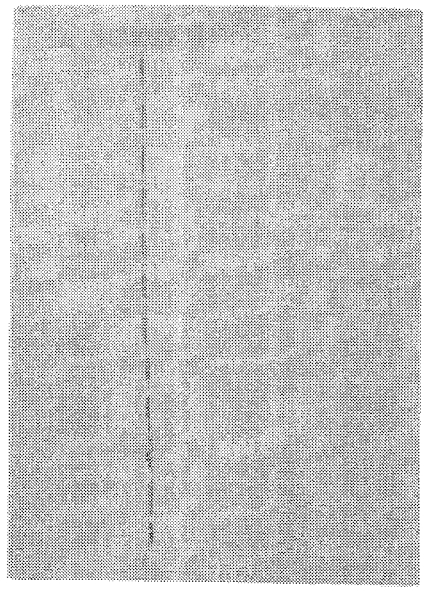
1 2 3 4 5 6 7 8 9 10 11 12
1- N0204E
2- N98
3- N0127E
4- N0135E
5- N045E
6- N1937
7- Hst-36
8- N10
9- N47
10- Hst-33
11- Hst-34
12- Hst-35

1- E. coli HB101 cell lysate

2- Purified Haemophilus e protein

3- HB101(pPX504) cell lysate

4- Molecular weight standards

1- HB101(pPX513) cell lysate

2- Molecular weight standards

3- Purified Haemophilus e protein

```
                                      ATGAAAACAACGTTAAAAATGACCGCACTTGCG
                                      MetLysThrThrLeuLysMetThrAlaLeuAla

GCTCTTTCTGCTTTTGTTTTAGCTGGCTGTGGTTCACACCAAATGAAATCAGAAGAACAT
AlaLeuSerAlaPheValLeuAlaGlyCysGlySerHisGlnMetLysSerGluGluHis

GCAAATATGCAATTACAACAACAAGCGGTGCTTGGATTAAACTGGATGCAAGATTCTGGC
AlaAsnMetGlnLeuGlnGlnGlnAlaValLeuGlyLeuAsnTrpMetGlnAspSerGly

GAATATAAAGCATTAGCTTATCAAGCGTACAATGCGGCAAAAGTTGCATTTGATCACGCA
GluTyrLysAlaLeuAlaTyrGlnAlaTyrAsnAlaAlaLysValAlaPheAspHisAla

AAAGTGGCAAAAGGTAAGAAAAAAGCGGTTGTGGCTGATTTAGATGAAACTATGTTAGAC
LysValAlaLysGlyLysLysLysAlaValValAlaAspLeuAspGluThrMetLeuAsp

AACAGCCCTTATGCTGGCTGGCAAGTTCAAAATAACAAACCATTCGATGGTAAAGATTGG
AsnSerProTyrAlaGlyTrpGlnValGlnAsnAsnLysProPheAspGlyLysAspTrp

ACTCGTTGGGTAGACGCACGTCAATCTCGTGCCGTTCCGGGTGCGGTAGAATTTAATAAT
ThrArgTrpValAspAlaArgGlnSerArgAlaValProGlyAlaValGluPheAsnAsn

TATGTAAACAGCCACAACGGTAAAGTGTTCTACGTAACAAACCGCAAAGACAGCACTGAA
TyrValAsnSerHisAsnGlyLysValPheTyrValThrAsnArgLysAspSerThrGlu

AAATCAGGCACTATCGATGATATGAAACGCTTAGGTTTCAATGGCGTGGAAGAATCTGCA
LysSerGlyThrIleAspAspMetLysArgLeuGlyPheAsnGlyValGluGluSerAla

TTTTATTTGAAAAAAGACAAATCAGCTAAAGCGGCTCGTTTTGCAGAAATTGAAAAACAA
PheTyrLeuLysLysAspLysSerAlaLysAlaAlaArgPheAlaGluIleGluLysGln

GGCTATGAAATCGTACTTTATGTAGGTGATAACTTAGATGACTTCGGTAATACCGTATAT
GlyTyrGluIleValLeuTyrValGlyAspAsnLeuAspAspPheGlyAsnThrValTyr

GGCAAATTAAACGCTGACCGCCGTGCATTCGTTGATCAAAACCAAGGCAAATTTGGTAAA
GlyLysLeuAsnAlaAspArgArgAlaPheValAspGlnAsnGlnGlyLysPheGlyLys

ACTTTCATCATGTTACCTAACGCAAACTACGGTGGCTGGGAAGGCGGTTTAGCTGAAGGG
ThrPheIleMetLeuProAsnAlaAsnTyrGlyGlyTrpGluGlyGlyLeuAlaGluGly

TATTTCAAAAAAGATACACAAGGCCAAATCAAAGCTCGTTTAGATGCAGTACAAGCTTGG
TyrPheLysLysAspThrGlnGlyGlnIleLysAlaArgLeuAspAlaValGlnAlaTrp

GATGGTAAATAA
AspGlyLysEnd
```

FIG. 6

1
Cys-Gly-Ser-His-Gln-Met-Lys-Ser-Glu-Glu-His-Ala-Asn-Met-Gln-Leu-Gln-Gln-Ala

21
Val-Leu-Gly-Leu-Asn-Trp-Met-Gln-Asp-Ser-Gly-Glu-Tyr-Lys-Ala-Leu-Ala-Tyr-Gln-Ala

41
Tyr-Asn-Ala-Ala-Lys-Val-Ala-Phe-Asp-His-Ala-Lys-Val-Ala-Lys-Gly-Lys-Lys-Lys-Ala

61
Val-Val-Ala-Asp-Leu-Asp-Glu-Thr-Met-Leu-Asp-Asn-Ser-Pro-Tyr-Ala-Gly-Trp-Gln-Val

81
Gln-Asn-Asn-Lys-Pro-Phe-Asp-Gly-Lys-Asp-Trp-Thr-Arg-Trp-Val-Asp-Ala-Arg-Gln-Ser

101
Arg-Ala-Val-Pro-Gly-Ala-Val-Glu-Phe-Asn-Asn-Tyr-Val-Asn-Ser-His-Asn-Gly-Lys-Val

121
Phe-Tyr-Val-Thr-Asn-Arg-Lys-Asp-Ser-Thr-Glu-Lys-Ser-Gly-Thr-Ile-Asp-Asp-Met-Lys

141
Arg-Leu-Gly-Phe-Asn-Gly-Val-Glu-Ser-Ala-Phe-Tyr-Leu-Lys-Lys-Asp-Lys-Ser-Ala

FIG. 7A

161
Lys-Ala-Ala-Arg-Phe-Ala-Glu-Ile-Glu-Lys-Gln-Gly-Tyr-Gly-Ile-Val-Leu-Tyr-Val-Gly

181
Asp-Asn-Leu-Asp-Asp-Phe-Gly-Asn-Thr-Val-Tyr-Gly-Lys-Leu-Asn-Ala-Asp-Arg-Arg-Ala

201
Phe-Val-Asp-Gln-Asn-Gln-Gly-Lys-Thr-Phe-Ile-Met-Leu-Pro-Asn-Ala-Asn

221
Tyr-Gly-Gly-Trp-Glu-Gly-Gly-Leu-Ala-Glu-Gly-Tyr-Phe-Lys-Lys-Asp-Thr-Trp-Gly-Gln

241
Ile-Lys-Ala-Arg-Leu-Asp-Ala-Val-Gln-Ala-Trp-Asp-Gly-Lys

1- EcoRI Digest of Hib Eagan DNA

2- Lambda HindIII standards

3- EcoRI Digest of nontypable Hi HDG-85 DNA

4- EcoRI Digest of E coli DNA

VACCINES FOR NONTYPABLE *HAEMOPHILUS INFLUENZAE*

RELATED APPLICATION

This application is a continuation-in-part application of U.S. Ser. No. 07/320,971, filed Mar. 9, 1989, now abandoned. The teachings are incorporated by reference herein.

BACKGROUND

*Haemophilus influenzae* are divided into two groups of strains, typable and nontypable. Strains which possess a known capsule are typed by the serological reaction of the capsule with reference antisera. Types a–f have been identified. Strains which fail to react with any of the reference antisera are nontypable.

*H. influenzae* type b (Hib) is the most frequent cause of neonatal meningitis and other invasive infections in the United States (Fraser et al., 1974, *Am. J. Epidemiol.* 100:29–34). The major incidence of childhood meningitis occurs between the ages of one and five years. Sixty percent of the meningitis cases due to Hib occur in children under the age of two years (Fraser et al., supra).

It is now well established that nontypable *H. influenzae* also cause diseases including pneumonia, bacteremia, meningitis, postpartum sepsis, and acute febrile tracheobronchitis in adults (Murphy et al., 1985, *J. Infect. Diseases* 152:1300–1307). In addition, nontypable *H. influenzae* are a frequent etiologic agent of otitis media in children and young adults. Indeed, about 20 to 40% of all cases of otitis media can be attributed to *H. influenzae*. Children may experience multiple infections of the same organism since infection confers no long lasting immunity. Currently, chronic or repeat otitis media is treated by administration of antibiotics and, if necessary, by drainage of the inner ear. *H. influenzae* strains have also been implicated as a primary cause of sinusitis (Cherry J. D. and J. P. Dudley, 1981, in Textbook of Pediatric Infectious Diseases, Feigin and Cherry eds., pp 103–105). Additionally, nontypable *H. influenzae* cause neonatal sepsis.

Antiserum produced against the capsular polysaccharide of Hib, polyribosyl ribitol phosphate (PRP), has been shown to be bactericidal and protective against Hib (Smith et al., 1973, *Pediatrics* 52:637–644; Anderson, et al., 1972, *J. Clin. Inv.* 51:31–88). Anti-PRP antibody, however, is ineffective against nontypable *H. influenzae* infection.

Currently available vaccines against *H. influenzae* are all directed against Hib. All are effective by eliciting anti-PRP antibody. Anti-PRP antibody, however, is ineffective against nontypable *H. influenzae*, which by definition lack the PRP capsule. There is a long recognized need for a vaccine that will protect against nontypable *H. influenzae*.

SUMMARY OF THE INVENTION

This invention pertains to the outer membrane protein "e" of *H. influenzae* and to peptides and proteins which have an epitope in common with protein "e". Protein "e" is a lipoprotein which has a molecular weight of about 28,000 daltons and an amino acid sequence as set forth in FIGS. 7A–7B. The invention also pertains to the use of protein "e" and peptides and proteins having protein "e" epitopes for vaccination against nontypable and typable *H. Influenzae*. The peptides and proteins can be used in univalent vaccines or in multivalent vaccines in conjunction with other antigens of typable or nontypable *H. influenzae* (e.g., as mixtures, fusion or conjugates therewith) or with antigens of other infectious bacteria, viruses or parasites. The peptides and proteins elicit biologically active (bactericidal and/or opsonic) antibody against *H. influenzae*. Importantly, protein "e" acts in synergy with other outer membrane proteins of *H. influenzae* in eliciting cross-reactive, bactericidal antibody responses, especially against nontypable strains of *H. influenzae*, and thus, the peptides or proteins of this invention are particularly effective when administered together with these proteins. In addition, antibody specific for epitopes of protein "e" can be used (either alone or in conjunction with antibody against epitopes of other outer membrane proteins) for passive immunization against *H. influenzae* and in diagnostic assays for the organism.

The invention also pertains to methods of producing native, purified protein "e", and to various vaccine formulations containing them. Protein "e" can be obtained by purification from *H. influenzae*. This invention also provides a method of isolating and purifying protein "e" in native lipoprotein form from *H. influenzae* by differential detergent extraction to provide an essentially endotoxin-free preparation without the use of agents considered harmful to humans. Protein "e" can also be produced by recombinant DNA techniques in lipidated or nonlipidated form or by protein synthesis. Epitopic oligopeptides and other fragments of protein "e" and analogues of these can be produced by recombinant DNA techniques, chemical synthesis or chemical or enzymatic cleavage. These peptides or proteins, in turn, can be fused or conjugated to other antigens of *H. influenzae* or to antigens of other microorganisms (bacteria, viruses, fungi or parasites) by chemical or genetic coupling techniques to produce multivalent antigenic conjugates and fusion peptides or proteins. The peptides or proteins can be modified for conjugation such as by addition of amino acids or other coupling groups. For vaccination, the peptides or proteins, in any of the forms described, can be formulated in pharmaceutically acceptable vehicles with optional additives such as adjuvants.

The invention also pertains to isolated nucleic acid sequences which encode the native protein "e" or any of the various peptidic or proteinaceous derivatives of the protein "e". The sequences can be incorporated into appropriate expression systems for production of protein "e" or any of the derived peptides and proteins of this invention. In addition, the gene fragments or oligonucleotides can be used as probes in nucleic acid hybridization assays.

BRIEF DESCRIPTION OF THE FIGURES

FIG. 2 (a and b) shows the results of an immunoblot analysis of the reactivity of antibodies against protein "e" with isolates of nontypable *H. influenzae*.

FIGS. 6A–6B shows DNA sequence of the coding region of the protein "e" gene from *H. influenzae* and derived amino acid sequence.

FIGS. 7A–7B shows amino acid sequence of the protein "e". The amino acid sequence of the mature protein "e" shown above is derived from the DNA sequence. The underlined sequence has been confirmed by amino acid sequencing of the peptides obtained from digestion of the purified "e" protein with several endoproteinases.

DETAILED DESCRIPTION OF THE INVENTION

Figure 1:
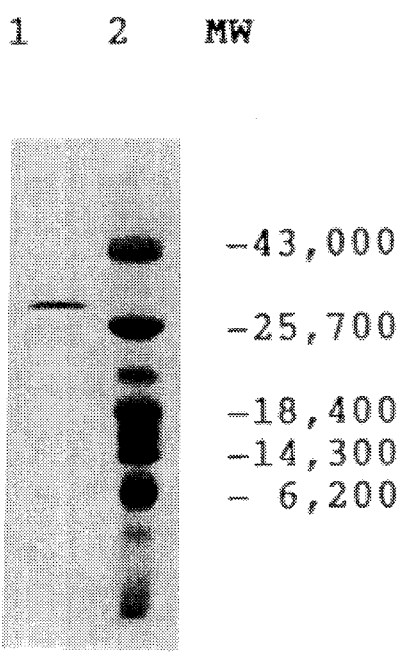
FIG. 1 shows the analysis of purified protein "e" by sodium dodecyl sulfate polyacrylamide gel electrophoresis.

Protein "e" is an outer membrane protein of *H. influenzae* which has a molecular weight of about 28,000 daltons and an amino acid sequence as shown in FIGS. 7A–7B. It has now been found that protein "e" exists as a lipoprotein in association with the outer membrane-cell wall complex of the bacteria.

Protein "e" has several properties which make it (and peptides and proteins having epitopes of protein "e") especially valuable for vaccination against nontypable *H. influenzae*. Protein "e" is capable of eliciting a bactericidal immune response against nontypable *H. influenzae*. Importantly, protein "e" is highly conserved among *H. influenzae* strains. The protein has been detected both by sodium dodecyl sulfate polyacrylamide gel electrophoresis (SDS-PAGE) and Western Blot analysis in all *H. influenzae* strains tested, and in addition, monoclonal antibody data indicate that the protein is highly conserved. Thus, the protein can induce an immune response against different strains of nontypable *H. influenzae*. Further, protein "e" elicits bactericidal antibodies which act in synergy with antibodies against other outer membrane proteins of *H. influenzae*. Because of this, the protein can be used in conjunction with other outer membrane proteins to induce a more potent bactericidal response.

This invention encompasses substantially pure protein "e" and peptides and proteins having epitopes of protein "e". The peptides or proteins bear a common epitope with protein "e" (and thus are immunologically crossreactive therewith). They can include fragments or oligopeptides containing epitopes of protein "e" as described below. The amino acid sequence of protein "e" has been determined and is shown in FIGS. 7A–7B. The peptides and proteins of this invention comprise any peptide or protein having at least a portion of the amino acid sequence depicted in FIGS. 7A–7B or any biologically equivalent sequences. Altered sequences include sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include glycine, alanine, leucine, isoleucine, valine, proline, phenylalanine, tryptophan and methionine. The polar neutral amino acids include serine, threonine, cysteine, tyrosine, asparagine, and glutamine. The charged (basic) amino acids include arginine, lysine and histidine. The negatively charged (acidic) amino acids include aspartic and glutamic acid.

The peptides and proteins of this invention also include fragments or oligopeptides having epitopes of protein "e" represented within the sequence or any analogues of such fragments or epitopes. In addition, any of the peptides and proteins can be modified for conjugation to other molecules, e.g. by the attachment of coupling groups such as the amino acids cysteine and lysine or other linking groups.

As described in detail below, protein "e" and the peptides and proteins of this invention can be used in many different forms, (e.g. alone, in mixtures or as conjugates and fusions) in vaccines and in diagnostic methods. For these purposes, the peptides and proteins can be produced by isolation from *H. influenzae*, by chemical synthesis, or by expression as recombinant molecules. The methods of using the peptides and proteins of this invention and the techniques for their production are discussed below.

Purification of Protein "e"

Native protein "e" can be purified from *H. influenzae* by a procedure of differential detergent extraction. The procedure is based on the use of sulfobetaine detergents which can selectively extract outer membrane proteins of *H. influenzae*. The procedure does not involve the use of denaturants and reducing agents such as sodium dodecylsulfate and 2-mercaptoethanol, respectively, (see Munson et al., 1984, *Infect. Immun.* 49:544–49) which can destroy important antigenic epitopes of the protein and which are not widely accepted as safe for administration to humans.

The procedure entails first obtaining outer membrane components of *H. influenzae* cells. Outer membrane components can be prepared from a total cell membrane fraction. Total membrane fractions are typically prepared by differential sedimentation after disruption of *H. influenzae* cells by methods such as sonication, grinding, or expulsion from a french press or other homogenization device. The total membrane fraction is then fractionated into inner and outer membranes by density gradient sedimentation or by differential solubilization of the inner membrane constituents with certain detergents such as polyoxyethyleneoctylphenol (Triton X-100™) or N-lauroyl sarcosine, sodium salt (sarcosyl). In the preferred embodiment, outer cell membrane components are prepared by differential solubilization of inner membranes in 0.1–2 %(w/v) Triton X-100™ in 10 mM HEPES-NaOH 1 mM $MgCl_2$, pH 7.4. This extraction is typically performed twice.

As an alternate source of outer membrane components, a culture medium of *H. influenza* cells can be used. The medium contains shed components (called "blebs") of the outer membrane of the bacteria. See Loeb, M. R. (1987) *Infection and Immunity* 55(11):2612–2618.

A subfraction of the preparation of outer cell membrane components which is enriched in protein "e" can be produced by extraction with an aqueous solution of 0.1–2.0% (preferably 1%) sarcosyl at pH 8.0. This extraction is typically performed two or three times and it removes a major protein component as well as other materials.

Solubilization of the protein "e" from the outer membrane-cell wall complex can then be achieved by a two-step differential solubilization with sulfobetaine detergents. In the first step, an aqueous solution of 0.1–10%, typically 0.1–2% (w/v) dodecylsulfobetaine (Zwittergent™ 3–12) is used to remove outer membrane proteins other than protein "e". Preferably, a 1% solution is used and the extraction is usually performed 2–3 times. The residual insoluble components are then extracted with an aqueous solution of tetradecyl- or hexadecylsulfobetaine (Zwittergent™ 3–14 or 3–16) under the same conditions. This extraction results in the solubilization of protein "e".

After solubilization, further purification of protein "e" can be achieved by standard methods including ion exchange, molecular sieve, hydrophobic, reverse phase or adsorption (e.g. hydroxylapatite) chromatography, affinity chromatography, chromatofocusing, isoelectric focusing and preparative electrophoresis.

Protein "e" purified by this method is substantially free of bacterial endotoxin and is suitable for administration to humans. The purified preparation of protein "e" can be formulated alone as a vaccine for *H. influenzae* or in a mixture with antigens of other organisms implicated in otitis media. If desired, the protein can be fragmented by standard chemical or enzymatic techniques to produce antigenic segments.

Preparation of the peptides and proteins by chemical synthesis

The peptides and proteins of this invention can be chemically synthesized according to the amino acid sequence shown in FIGS. 7A–7B or variations of this sequence as described above. Any of the standard chemistries for solid or liquid phase synthesis of peptides and proteins may be used. Chemical synthesis may be particularly suitable for production of oligopeptides containing epitopes of protein "e".

Preparation of the peptides and proteins by recombinant DNA techniques

Protein "e" and the peptides and proteins which share epitopes of protein "e" can be produced by recombinant DNA techniques. In general, these entail obtaining by synthesis or isolation a DNA sequence which encodes the derived peptide or protein and introducing it into an appropriate vector/host expression system where it is expressed. The DNA can consist of the gene encoding protein "e" or any segment of the gene which encodes a useful segment of the protein "e". The DNA can be fused to DNA encoding other antigens of *H. influenzae* or antigens of other bacteria, viruses, parasites or fungi to create genetically fused (sharing a common peptide backbone) multivalent antigens. For example, protein "e" can be fused to other outer membrane proteins (or fragments or epitopes thereof) of *H. influenzae* to yield fusion proteins comprising multiple outer membrane protein determinants.

Genetic engineering techniques can also be used to characterize, modify and/or adapt the encoded peptides or proteins. For example, site directed mutagenesis of the gene encoding protein "e" can be used to identify regions of the protein responsible for generation of protective antibody responses (e.g., bactericidal or opsonic epitopes). These techniques can also be used to modify the protein in regions outside the protective domains, for example, to increase the solubility of the protein to allow easier purification.

Obtaining DNA encoding protein "e"

DNA encoding protein "e" or fragments thereof, can be synthesized chemically according to the nucleotide sequence shown in FIGS. 6A–6B. Several techniques are available for synthesizing DNA of desired nucleotide sequences. See, e.g., Matteucci et al., *J. Am. Chem. Soc.* (1981) 103:3185; Alvarado-Urbina et al., *Science* (1980) 214:270. A preferred technique for synthesis of DNA segments is the β-cyanoethyl phophoramidite chemistry. See e.g., Sinha, N. D. et al., *Nucleic Acids Research* 13:4539 (1984). The synthesized DNA can be adapted for insertion into appropriate vectors by techniques described below for isolated DNA.

As an alternative to chemical synthesis, DNA encoding protein "e" can be isolated from *Haemophilus influenzae*. Any *H. influenzae* strain can serve as the source for the protein "e" gene. Since many *H. influenzae* strains contain no detectable plasmids or inducible prophages, the protein "e" gene is probably chromosomal, thus, the gene must be isolated from *H. influenzae* chromosomal DNA. In the remainder of this section, DNA encoding an *H. influenzae* gene will be referred to as "Hi DNA", and DNA encoding protein "e" sequences will be referred to as "protein "e" DNA".

In order to generate Hi DNA fragments, the Hi DNA can be cleaved at specific sites with various restriction enzymes. Alternatively, one may use low concentrations of DNase I to fragment the DNA, or the DNA can be physically sheared, for example, by sonication. The linear DNA fragments can then be separated according to size by standard techniques such as-agarose and polyacrylamide gel electrophoresis, column chromatography (e.g., molecular sieve or ion exchange chromatography) or velocity sedimentation in sucrose gradients.

Any restriction enzyme or combination of restriction enzymes may be used to generate the Hi DNA fragment(s) containing the protein "e" sequence provided the enzyme(s) does not destroy a desired property (e.g., immunopotency) of the protein "e" gene product. For example, an epitope of a protein can consist of from about 7 to about 14 amino acids. Thus, a protein of the size of the protein "e" may have many discrete epitopes and therefore, many partial protein "e" gene sequences can code for an epitope. Consequently many combinations of restriction enzymes can be used to generate DNA fragments which encode amino acid sequences corresponding to different antigenic determinants of protein "e".

Once the DNA fragments are generated, identification of the specific DNA fragment containing the protein "e" gene can be accomplished in a number of ways.

The DNA sequences containing the protein "e" gene can be identified by hybridization with a synthetic oligonucleotide probe. Redundant synthetic oligonucleotide probes can be constructed based upon the amino acid sequence of the substantially pure protein "e". These synthetic probes can be radiolabeled with $^{32}$P-adenosine triphosphate and used to screen Hi DNA libraries for clones containing protein "e"-specific gene sequences (see Anderson et al., 1983, *Proc. Nat'l Acad. Sci. U.S.A.* 80:6838–42).

Alternatively, the protein "e" DNA may be identified and isolated after insertion into a cloning vector in a "shotgun" approach. A large number of vector-host systems known in the art may be used. Vector systems may be either plasmids or modified viruses. Suitable cloning vectors include, but are not limited to the viral vectors such as λ vector system λgt11, λgt λWES.tB, Charon 4, and plasmid vectors such as pBR322, pBR325, pACYC177, pACYC184, pUC8, pUC9, pUG18, pUC19, pLG339, pR290, pK37, pKC101 and other similar systems. The vector system must be compatible with the host cell used. Recombinant molecules can be introduced into cells via transformation, transfection or infection.

When Hi DNA containing a protein "e" gene or gene fragment is inserted into a cloning vector and used to transform appropriate host cells many copies of the protein "e" gene or gene fragment can be generated. This can be accomplished by ligating the Hi DNA fragment into a cloning vector which has complementary cohesive termini. If, however, the complementary-restriction sites are not present, the ends of the DNA molecules may be modified.

Such modification includes producing blunt ends by digesting back single-stranded DNA termini or by filling the single-stranded termini so that the ends can be blunt-end-ligated. Alternatively, any site desired may be produced by ligating nucleotide sequences (linkers) onto the DNA termini. These ligated linkers may comprise specific chemically synthesized oligonucleotides encoding restriction site recognition sequences. For example, according to the DNA modification procedure of Maniatis, (see Maniatis et al., 1982, Molecular Cloning, Cold Spring Harbor Laboratory, pp. 107–114) sheared DNA is treated with a restriction methylase (for example, M. EcoRI) and ligated to synthetic DNA linkers which encode a restriction site for that enzyme. The DNA is then treated with restriction enconuclease to cleave the terminal linkers (but not the modified internal restriction sites) and ligated to the appropriate vector arms. In an alternative method, the cleaved vector and protein "e" DNA fragment may be modified by homopolymeric tailing.

Recombinant protein "e" can be produced as a lipidated or nonlipidated protein. For example, by using the intact protein "e" gene, including its native leader-encoding sequence, a lipidated protein "e" can be produced in host cells such as E. coli. To produce a nonlipidated protein "e", the leader-encoding segment of the protein "e" gene can either be removed or be replaced by a segment which encodes a leader sequence which does not specify a site for fatty acylation in the host cell.

Identification of a cloned protein "e" DNA can be accomplished by establishing a chromosomal gene bank of *H. influenzae* in a vector system and screening individual clones for the production of protein "e" or peptide or protein derived from protein "e" by any of the methods described herein, including, but not limited to specific reaction with polyclonal or monoclonal antibodies against protein "e" epitopes.

DNA Expression systems

A variety of host-vector systems can be used to express the peptides and proteins of this invention. Primarily the vector system must be compatible with the host cell used. Host-vector systems include but are not limited to the following: bacteria transformed with bacteriophage DNA, plasmid DNA or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

In order to obtain efficient expression of the DNA, a promoter must be present in the expression vector. RNA polymerase normally binds to the promoter and initiates transcription of a gene or a group of linked genes and regulatory elements (called an operon). Promoters vary in their "strength", i.e., their ability to promote transcription. It is desirable to use strong promoters in order to obtain a high level of transcription and, hence, a high level of DNA expression. Depending upon the host cell system any one of a number of suitable promoters can be used. For instance, for *E. coli*, its bacteriophages or plasmids, promoters such as the lac promoter, trp promoter, recA promoter, ribosomal RNA promoter, and $P_R$ or $P_L$ promoters of coliphage lambda and others including but not limited to lacUV5, ompF, bla, lpp and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted DNA.

Bacterial host cells and expression vectors may be chosen which inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promoter of lambda can be induced by an increase in temperature in host cells containing a temperature sensitive lambda repressor, e.g., cI857. In this way, greater than 95% of the promoter-directed transcription may be inhibited in uninduced cells. Thus, expression of the recombinant peptide or protein can be controlled. This is important if the expression product of the DNA is lethal or detrimental to the host cells. In such cases, transformants may be cultured under conditions such that the promoter is not induced; then, when the cells reach a suitable density in the growth medium, the promoter can be induced for production of the protein.

One such promoter/operator system is the so-called "tac" or trp-lac promoter/operator system (Russell and Bennett, 1982, *Gene* 20:2312; DeBoer, European Patent Application, 67, 540 filed May 18, 1982). This hybrid promoter is constructed by combining the −35 b.p. (−35 region) of the trp promoter and the −10 b.p. (−10 region or Pribnow box) of the lac promoter (the sequences of DNA which are the RNA polymerase binding site). In addition to maintaining the strong promoter characteristics of the tryptophan promoter, tac is also controlled by the lac repressor.

When cloning in a eucaryotic host cell, enhancer sequences (e.g., the 72 bp tandem repeat of SV40 DNA or the retroviral long terminal repeats or LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have a remarkable ability to function upstream from, within, or downstream from eucaryotic genes; therefore, the position of the enhancer sequence with respect to the inserted DNA is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Any of the methods described for the insertion of DNA into an expression vector can be used to ligate a promoter and other genetic control elements into specific sites within the vector. *H. influenzae* sequences for expression can be ligated into an expression vector at a specific site in relation to the vector promoter and control elements so that when the recombinant DNA molecule is introduced into a host cell the foreign genetic sequence can be expressed (i.e., transcribed and translated) by the host cell.

The recombinant DNA vector can be introduced into appropriate host cells (bacteria, virus, yeast, mammalian cells or the like) by transformation, transduction or transfection (depending upon the vector/host cell system). Host cells containing the vector are selected based upon the expression of one or more appropriate gene markers normally present in the vector, such as ampicillin resistance or tetracycline resistance in pBR322, or thymidine kinase activity in eucaryotic host systems. Expression vectors may be derived from cloning vectors, which usually contain a marker function. Such cloning vectors may include, but are not limited to the following: SV40 and adenovirus, vaccinia virus vectors, insect viruses such as baculoviruses, yeast vector, bacteriphage vectors such as lambda gt-WES-lambda B, Charon 28, Charon 4A, lambda gt-1-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col El, pSC101, pBR313, pML21, RSF2124, pCR1, RP4, pBR328 and the like.

Transfer of drug resistance factors between *H. influenzae* and *E. coli* via conjugation (Stuy, 1979, *J. Bact.* 139:520–529); and transformation (Mann, 1979, *Plasmid* 2:503–505) and cloning of Haemophilus chromosomal genes in *E. coli* (Deich et al., 1988, *J. Bact.* 170:489–498; Mann et al., 1980, *Gene* 3:97–112) indicate that at least some genes can be efficiently expressed in both organisms; and that the basic mechanisms of transcriptional and translational control may be similar.

Expression vectors containing the DNA inserts can be identified by three general approaches: (1) DNA-DNA hybridization using probes comprising sequences that are homologous to the inserted gene; (2) presence or absence of "marker" gene functions (e.g., resistance to antibiotics, transformation phenotype, thymidine kinase activity, etc.); and (3) expression of inserted sequences based on the physical immunological or functional properties of the gene product.

Once a putative recombinant clone which expresses a protein "e" sequence is identified, the gene product can be analyzed as follows. Immunological analysis is especially important because the ultimate goal is to use the gene products in vaccine formulations and/or as antigens in diagnostic immunoassays. The peptide or protein should be immunoreactive. This reactivity may be demonstrated by standard immunological techniques, such as radio-immuno-precipitation, radioimmune competition, ELISA or immunoblots.

Once the gene product is identified as protein "e" or a protein-e-derived peptide or protein, it can be isolated and purified by standard methods including chromatography (e.g., ion exchange, affinity, and sizing column chromatography), centrifugation, differential solubility, or by any other standard techniques for the purification or proteins. Several techniques exist for purification of heterologous protein from prokaryotic cells. See e.g., Olson, U.S. Pat. No. 4,518, 526, Whetzel, U.S. Pat. No. 4,599,197 and Hung et al., U.S. Pat. No. 4,734,362. The purified preparation however produced should be substantially free of host toxins which might be harmful to humans. In particular, when expressed in gram negative bacterial host cells such as *E. coli*, the purified peptide or protein should be substantially free of endotoxin contamination.

Evaluating Immunopotency of the peptides and proteins

Experience with antibodies to the capsular polysaccharide of Hib PRP, shows that the ability of the antibodies to kill the bacteria in in vitro assays and/or to protect against challenge with Hib in animal model systems is closely correlated with the ability to elicit a protective immune response in human infants.

Anti-protein "e" antibodies elicited in response to the peptides and proteins of this invention can be tested using similar in vitro assay systems and animal model systems to demonstrate the ability to kill *H. influenzae* cells and to protect in animal model systems from challenge with *H. influenzae*. The results from these systems should show a similar correlation with the potential of the protein "e" to elicit a protective immune response and to serve in a vaccine for human infants, children and adults.

An in vitro complement mediated bactericidal assay system (Musher et al., 1983, *Infect. Immun.* 39:297–304; Anderson et al., 1972, *J. Clin. Invest.* 51:31–38) which has been used previously for measuring bactericidal activity of antibodies to PRP and lipopolysaccharide (LPS) against *H. influenzae* can be used to determine whether or not antibody directed against a particular peptide protein or fragment thereof has bactericidal activity against nontypable *H. influenzae*. These assays can be performed against a relatively large number of clinical isolates of nontypable strains to determine whether a broad range of strains are killed.

Data on the ability of antibody to a particular peptide or protein to protect against *H. influenzae* can be obtained using the chinchilla otitis media animal model system. (Barenkamp et al., 1986, *Infect. Immun.* 52:572–78). In this animal model, chinchillas are challenged by inoculation of the inner ear canal with *H. influenzae*. An otitis media much like that seen in humans develops. Chinchillas, which have been immunized, either actively with outer membrane proteins of *H. influenzae*, or passively with antibody directed against these proteins are protected against aural challenge with *H. influenzae*. (Barenkamp et al., supra). This animal model system could be used to demonstrate the ability of antibody to protect against Hi.

Peptides or proteins derived from protein "e" can be evaluated for additive or synergistic biological activity (e.g. bactericidal and/or opsonic activity). As has been established, protein "e" evokes bactericidal antibodies which act synergistically with antibodies against other outer membrane proteins of *H. influenzae*. Additive or synergistic biological activity can be determined by diluting bactericidal antibodies so that they are no longer bactericidal against Hi and then testing the diluted antibodies in combination with other antibodies for additive or synergistic activity. Additive or synergistic biological activity is useful for a combination vaccine composed of protein "e" or a fragment or conjugate thereof, and other outer membrane proteins or fragments thereof.

Vaccines

The peptides and proteins of this invention can be used as immunogens in subunit vaccines for vaccination against nontypable *H. influenzae*. The vaccines can be used to prevent or reduce susceptibility to acute otitis media and other diseases caused by nontypable strains of the organism. The vaccines are useful to generally vaccinate children or adults against otitis media or they may be useful for children at risk of contracting otitis media (for example, children with a history of ear infection).

The peptides and proteins of this invention can be formulated as univalent and multivalent vaccines. Protein "e" itself can be used as produced or isolated by the methods described above.. The protein can be mixed, conjugated or fused with other antigens, including B or T cell epitopes of other antigens. In addition to its utility as a primary immunogen, protein "e" can be used as a carrier protein to confer or enhance immunogenicity of other antigens.

When a haptenic peptide of protein "e" is used, (i.e., a peptide which reacts with cognate antibodies, but cannot itself elicit an immune response), it can be conjugated to an immunogenic carrier molecule. For example, an oligopeptide containing one or more epitopes of protein "e" may be haptenic. Conjugation to an immunogenic carrier can render the oligopeptide immunogenic. Preferred carrier proteins for the haptenic peptides of protein "e" are tetanus toxin or toxoid, diphtheria toxin or toxoid and any mutant forms of these proteins such as $CRM_{197}$. Others include exotoxin A of Pseudomonas, heat labile toxin of *E. coli* and rotaviral particles (including rotavirus and VP6 particles). Alternatively, a fragment or epitope of the carrier protein or other immunogenic protein can be used. For example, the hapten can be coupled to a T cell epitope of a bacterial toxin. See U.S. patent application Ser. No. 150,688, filed Feb. 1, 1988, entitled "Synthetic Peptides Representing a T-Cell Epitope as a Carrier Molecule For Conjugate Vaccines", the teachings of which are incorporated herein.

The peptides or proteins of this invention can be administered as multivalent subunit vaccines in combination with other antigens of *H. influenzae*. For example, they may be administered in conjunction with oligo- or polysaccharide capsular components of *H. influenzae* such as polyribosyl-ribitolphosphate (PRP).

As mentioned, peptides and proteins having epitopes of protein "e" evoke bactericidal antibodies which act synergistically in killing *H. influenzae* with antibodies against other outer membrane proteins of *H. influenzae*. Thus, in an embodiment of the invention, protein "e" (or a peptide or protein having a common epitope) is administered in conjunction with other outer membrane proteins of *H. influenzae* (or peptides or proteins having epitopes thereof) to achieve a synergistic bactericidal activity. Particularly preferred outer membrane proteins of *H. influenzae* are the 15,000-dalton peptidoglycan-associated outer membrane lipoprotein (PAL) and the 15,000-dalton Haemophilus lipoprotein PCP described by Deich, R. A. et al. (1988) *J. Bacteriol.* 170(2):489–498, the teachings of which are incorporated by reference herein. For combined administration with epitopes of other outer membrane proteins, the protein "e" peptide can be administered separately, as a mixture or as a conjugate or genetic fusion peptide or protein. For example, the PAL and PCP or any proteins, peptides or epitopes derived from them, can be administered as a mixture or as a conjugate or fusion with a protein "e" or a protein "e" derived peptide or protein. The conjugates can be formed by standard techniques for coupling proteinaceous materials. Fusions can be expressed from fused gene constructs prepared by recombinant DNA techniques as described.

Protein "e" or any derived peptides or proteins can be used in conjunction with antigens of other organisms (e.g. encapsulated or nonencapsulated, bacteria, viruses, fungi and parasites). For example, protein "e" can be used in conjunction with antigens of other microorganisms implicated in otitis media. These include *Streptococcus pneumoniae, Streptococcus pyogenes,* group A, *Staphylococcus aureus,* respiratory syncytial virus and *Branhamella catarrhalis.*

In formulating the vaccine compositions with the peptide or protein, alone or in the various combinations described, the immunogen is adjusted to an appropriate concentration and formulated with any suitable vaccine adjuvant. Suitable adjuvants include, but are not limited to: surface active substances, e.g., hexadecylamine, octadecylamine, octadecyl amino acid esters, lysolecithin, dimethyl-dioctadecylammonium bromide), methoxyhexadecylgylcerol, and pluronic polyols; polyamines, e.g., pyran, dextransulfate, poly IC, carbopol; peptides, e.g., muramyl dipeptide, dimethylglycine, tuftsin; oil emulsions; and mineral gels, e.g., aluminum hydroxide, aluminum phosphate, etc. and immune stimulating complexes. The immunogen may also be incorporated into liposomes, or conjugated to polysaccharides and/or other polymers for use in a vaccine formulation.

The vaccines can be administered to a human or animal in a variety of ways. These include intradermal, intramuscular, intraperitoneal, intravenous, subcutaneous, oral and intranasal routes of administration.

Live vaccines

The peptide and proteins of this invention can be administered as live vaccines. To this end, recombinant microorganisms are prepared that express the peptides or proteins. The vaccine recipient is inoculated with the recombinant microorganism which multiplies in the recipient, expresses the protein "e" peptide or protein and evokes a immune response to *H. influenzae*. Preferred live vaccine vectors are pox viruses such as vaccinia (Paoletti and Panicali, U.S. Pat. No. 4,603,112) and attenuated Salmonella strains (Stocker, U.S. Pat. No. 4,550,081).

Live vaccines are particularly advantageous because they lead to a prolonged stimulus which can confer substantially long-lasting immunity. When the immune response is protective against subsequent *H. influenzae* infection, the live vaccine itself may be used in a preventative vaccine against *H. influenzae*.

Multivalent live vaccines can be prepared from a single or a few recombinant microorganisms that express different epitopes of *H. influenzae* (e.g., other outer membrane proteins such as PAL and PCP or epitopes thereof). In addition, epitopes of other pathogenic microorganisms can be incorporated into the vaccine. For example, a vaccinia virus can be engineered to contain coding sequences for other epitopes in addition to those of *H. influenzae*. Such a recombinant virus itself can be used as the immunogen in a mulivalent vaccine. Alternatively, a mixture of vaccinia or other viruses, each expressing a different gene encoding for different epitopes of outer membrane proteins of *H. influenza* and/or epitopes of other disease causing organisms can be formulated as a multivalent vaccine.

An inactivated virus vaccine may be prepared. Inactivated vaccines are "dead" in the sense that their infectivity has been destroyed, usually by chemical treatment (e.g., formaldehyde treatment). Ideally, the infectivity of the virus is destroyed without affecting the proteins which carry the immunogenicity of the virus. In order to prepare inactivated vaccines, large quanitites of the recombinant virus expressing the desired epitopes are grown in culture to provide the necessary quantity of relevant antigens. A mixture of inactivated viruses express different epitopes may be used for the formulation of "multivalent" vaccines. In certain instances, these "multivalent" inactivated vaccines may be preferable to live vaccine formulation because of potential difficulties arising from mutual interference of live viruses administered together. In either case, the inactivated virus or mixture of viruses should be formulated in a suitable adjuvant in order to enhance the immunological response to the antigens. Suitable adjuvants include: surface active substances, e.g., hexadecylamine, octadecyl amino acid esters, octadecylamine, lysolecithin, dimethyl-dioctadecylammonium bromide, N, N-dicoctadecyl-N'-N'bis (2-hydroxyethyl-propane diamine), methoxyhexadecylglycerol, and pluronic polyols; polyamines, e.g., pyran, dextransulfate, poly IC, carbopol; peptides, e.g., muramyl dipeptide, dimethylglycine, tuftsin; oil emulsions; and mineral gels, e.g., aluminum hydroxide, aluminum phopshate, etc.

Passive Immunity and Anti-Idiotypic Antibodies

The bactericidal antibodies induced by protein "e" epitopes can be used to passively immunize an individual against *H. influenzae*. Passive immunization confers short-term protection for a recipient by the administration of the pre-formed antibody. Passive immunization can be used on an emergency basis for special risks, e.g., young children exposed to contact with bacterial meningitis patients.

The peptides and proteins of this invention can be used to produce polyclonal or monoclonal antibodies for use in passive immunotherapy against *H. influenzae*. Human immunoglobulin is preferred because heterologous immunoglobulin may provoke a deleterious immune response to its foreign immunogenic components. Polyclonal antisera can be obtained from individuals immunized with the peptides or proteins in any of the forms described. Immunoglobulin fraction can then be enriched. For example, immunoglobulins specific for epitopes of protein "e" can be enriched by immunoaffinity techniques employing the peptides or proteins of this invention. The antibody can be specifically adsorbed from antisera onto an immunoadsorbent containing epitopes of protein "e" and then eluted from the immunoadsorbent as an enriched fraction of immunoglobulin.

Monoclonal antibodies against epitopes of protein "e" can be made by standard somatic cell fusion techniques of Kohler and Milstein, *Nature* 256:495 (1975) or similar procedures employing different fusing agents. Briefly, the procedure is as follows: an animal is immunized with protein "e" or immunogenic fragments or conjugates thereof. For example, haptenic oligopeptides of protein "e" can be conjugated to a carrier protein to be used as an immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired antibody.

Human hybridomas which secrete human antibody can be produced by the Kohler and Milstein technique. Although human antibodies are especially preferred for treatment of human, in general, the generation of stable human-human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See V. T. Oi et al., *Bio Techniques* 4(4):214–221 (1986); L. K. Sun et al., *Hybridoma* 5 (1986).

The monoclonal antibodies specific for protein "e" epitopes can be used to produce anti-idiotypic (paratope-specific) antibodies. See e.g., McNamara et al., Dec. 14, 1984, *Science, page* 1325; Kennedy, R. C. et al., (1986) *Science* 232:220. These antibodies resemble the protein "e" epitope and thus can be used as an antigen to stimulate an immune response against *H. influenzae*.

Diagnostic Assays

The peptides and proteins of this invention may be used as antigens in immunoassays for the detection of *H. influenzae* in various tissues and body fluids e.g., blood, spinal fluid, sputum, etc. A variety of immunoassay systems may be used. These include: radio-immunoassays, ELISA assays, "sandwich" assays, precipitin reactions, gel diffusion precipitin reactions, immunodiffusion assays, agglutination assays, fluorescent immunoassays, protein A immunoassays and immunoelectrophoresis assays.

In addition, nucleic acids having the nucleotide sequence of the gene encoding protein "e" (FIGS. 6A–6B) or any nucleotide sequences which hybridize therewith can be used as probes in nucleic acid hybridization assays for the detection of *H. influenzae* in various tissues or body fluids of patients. The probes may be used in any nucleic any type of hybridization assay including: Southern blots (Southern, 1975, *J. Mol. Biol.* 98:508); Northern blots (Thomas et al., 1980, *Proc. Nat'l Acad. Sci. U.S.A.* 77:5201–05); colony blots (Grunstein et al., 1975, *Proc. Nat'l Acad. Sci. U.S.A.* 72:3961–65), etc. Stringency of hybridization can be varied depending on the requirements of the assay.

The invention is further illustrated by the following examples.

Exemplification

I. Isolation of protein "e"

Isolation of Haemophilus Cell Envelopes

Cell envelopes were isolated from Hib strain Eagan cells grown on either brain heart infusion medium containing 10 µg/ml hemin and 1 µg/ml NAD (BHI/XV) or mMIC (modification of Herriott et al., *J. Bacteriol.*, 101:513–516 (1970)) media. Cells were harvested from liquid cultures by centrifugation at 10,000 x g, 4° C. for 10 minutes. The cell pellet was weighed and resuspended in 10 mM HEPES-NaOH (pH 7.4), 1 mM EDTA, with a volume equal to five times the wet weight of the cells. The cells were disrupted using a Gaulin homogenizer. The disrupted cell suspension was centrifuged at 10,000 x g for 5 minutes at 4° C. to remove unbroken cells and large debris. The supernatant fraction was saved and NaCl added to 0.5M. Cell membranes were pelleted by centrifugation at 100,000 x g for about 1 h at 4° C.

An outer membrane-cell wall complex was obtained by removing the inner membranes from the total membrane fraction by repeated extraction of the total membrane fraction with 2% Triton X-100 in 10 mM HEPES-NaOH, 1 mM MgCl$_2$, pH 7.4. The insoluble residue containing the outer membrane-cell wall complex was pelleted by centrifugation at 350,000 x g for 30 minutes at 4° C. This complex was then resuspended in 50 mM Tris-HCl, 5 mM Na$_2$EDTA, pH 8 and stored at 4° C.

Isolation of protein "e" from Haemophilus Cell Envelopes

Contaminating proteins were solubilized from *H. influenzae* cell envelopes by differential detergent extraction as follows. Cell envelopes prepared as described above were sequentially extracted twice with 1% sarcosyl in 50 mM Tris-HCl, 5 mM Na$_2$EDTA, pH 8 and the insoluble material recovered by centrifugation at 350,000 x g for 30 minutes at 20° C., then twice with 1% Zwittergent™ 3–12 in the same buffer, 50 mM Tris-HCl, 5 mM Na$_2$EDTA, pH 8. The protein "e" was now solubilized from the insoluble residual outer membrane-cell wall material by extraction with 1% Zwittergent™ 3–14 in 50 mM Tris-HCl, 5 mM Na$_2$EDTA, pH 8. This extraction was repeated three times. The solubilized protein "e" containing fractions were pooled and passed through a DEAE column equilibrated with 50 mM Tris-HCl, 5 mM Na$_2$EDTA, pH 8. The protein "e" was not retained under these conditions but the major protein contaminants were retained. The fall-through fractions containing protein "e" were then passed over a hydroxylapatite column which had been equilibrated with 50 mM Tris-HCl, pH 8. The protein "e" was retained under these conditions. The hydroxylapatite column with the adsorbed protein "e" was then washed with one column volume of 50 mM Tris-HCl, pH 8. The protein "e" was eluted from the hydroxylapatite with 1% Zwittergent™ 3–14 in 0.3M dibasic phosphate, pH 8. Fractions containing protein "e" were pooled, concentrated by diafiltration, and precipitated with ethanol. The precipitated protein "e" was then solubilized again by differential detergent extraction. The precipitate was first extracted with 1% octylglucoside in 50 mM Tris-HCl, pH 8 and the insoluble protein "e" remained in the precipitate. The protein "e" was then solubilized with 1% Zwittergent™ 3–14 in 50 mM Tris-HCl, 5 mM Na$_2$EDTA, pH 8. More preferably, the fall through fractions from the DEAE column were passed over an S Sepharose™ (Pharmacia) fast flow column (cation exchange column), previously equilibrated with 50 mM Tris-HCl, 5mM Na$_2$EDTA (pH8), containing 0.1% Zwittergent™ 3–14. The protein "e" adsorbed to the column and was eluted with a 0–0.5M NaCl gradient in the same buffer. Protein "e" prepared as described above is substantially pure and essentially free of endotoxin could be further concentrated as previously described or used as eluted.

Characterization of protein "e" by Amino Acid Composition and Sequence

Amino acid analysis was performed according to the procedure of Simpson et al. (*J. Biol. Chem.*, 251:1936–1940 (1976)). Hydrolysis was accomplished by heating 0.5–1 mg of protein in 0.1 ml of 4N methane sulfonic acid under vacuum in a thick-walled sealed glass tube at 150° C. for 90 minutes. The quantity of each amino acid is obtained by comparison of the areas under the various peaks with areas obtained using known quantities of standard amino acids. Results obtained are illustrated in Table 1.

Samples were prepared for analysis by SDS-PAGE by adjusting them to 0.1M Tris-HCl, pH 7.0, 25 mM dithiothreitol, and 2% SDS with 5X concentrated sample buffer, then heating for 5 minutes at 100° C. Prior to electrophoresis all samples were adjusted to 6% (w/v) sucrose and 0.001% bromophenol blue. Most routine analyses were performed using the Bio-Rad Mini Protein Gel System (Redmond, Calif.). Gels were 1.5 mm thick and the separating gel contained 15% acrylamide with an acrylamide to bis ratio of 30:0.8, 0.375M Tris-HCl (pH 8.8) and 0.1% SDS. The stacking gel contained 4.8% acrylamide with the same ratio of acrylamide to bis, 125 mM Tris, HCl (pH 7.0), and 0.1% SDS per gel. Following electrophoresis gels were stained for at least 1 hour with 0.125% (w/v) Coomasie blue in ethanol: acetic acid: water (5:1:5), then destained in the same solvent system without the blue dye. Pre-stained low molecular weight standards which included the following: ovalbumin, 43,000; alpha-chymotrypsinogen, 25,700; Beta-lactoglobulin, 18,400; lysozyme, 14,300; bovine trypsin inhibitor, 6,200; insulin (A and B Chains), 2,300 and 3,400 (BRL, Bethesda, Md.) were used to assist in the determination of the relative molecular weight of the protein "e".

Further purification of protein "e" can be achieved by standard methods such as ion exchange chromatography, molecular sieving, hydrophobic or reserve phase chromatography, chromatofocusing, gel electrophoresis and the like.

Substantially pure protein "e" was analyzed in an SDS-PAGE system to determine the relative molecular weight of the reduced and denatured form of the protein and to assess its purity (FIG. 1). A sample purified "e" protein (3ug) was analyzed in a 15% SDS-PAGE system and stained with Coomassie blue. Lane 1, purified "e" protein; Research Laboratories Life Technologies, Inc., which included ovalbumin, α-chymotrypsinogen, β-lactoglobulin, lysozyme, bovine trypsin inhibitor, and insulin (A and B chains). The reported respective molecular weights of the standards and 43,000; 25,700; 18,400; 6,200; 2,300 and 3,400.

TABLE 1

AMINO ACID COMPOSITION OF THE *H. INFLUENZAE* "e" PROTEIN

| Amino Acid | Analysis | |
|---|---|---|
| | Methane | Sulfonic Acid |
| Asp | 34 | (38) |
| Thr | 9 | (8) |
| Ser | 9 | (10) |
| Glu | 29 | (29) |
| Pro | 6 | (4) |
| Gly | 25 | (24) |
| Ala | 29 | (28) |
| Cys* | 0 | (1) |
| Val | 18 | (18) |
| Met* | 5 | (6) |
| Ile | 7 | (5) |
| Leu | 17 | (14) |
| Tyr | 11 | (12) |
| Phe | 12 | (12) |
| His | 4 | (4) |
| Lys | 26 | (26) |
| Trp | nd | (6) |
| Arg | 11 | (9) |

Values have been adjusted to nearest whole number and are expressed in terms of residues/proteins.
*Values given for these amino acids are from the respective digests. None of the forms for cysteine were observed even after performing acid oxidation, however, five (5) methionyl residues would be predicted using performic acid as well as methanesulfonic acid. Residues in ( ) are predicted from the available DNA sequence and peptide mapping.

Initial attempts at sequencing protein "e" using Edman chemistry failed to yield satisfactory results because of a blocked N-terminal residue. In order to obtain partial amino acid sequence information, it was necessary to enzymatically digest protein "e" with proteolytic enzymes to obtain peptide fragments that were amenable to sequence analysis.

Samples of the "e" protein (0.3 mg/mL) were incubated overnight with one of three proteases, endoproteinase Lys-C, Arg-C, or V8, at an enzyme to protein ratio of 1:100 at 37°

C. Peptides from these endoproteinase digests were obtained by reverse phase HPLC analysis. Samples (50–100μL) of each of the digests were analyzed on an Aquapore RP-300 column on the Applied Systems microbore HPLC with the detection wavelength set at 220 nm. Buffer A was 0.1% TFA and Buffer B was 95% acetonitrile in 0.1% gradient up to 40% Buffer B at 15 min, then a steeper gradient to 100% Buffer B at 17.5 min and continuing at 100%B for 2.5 min more. Fractions were collected by hand. Amino acid sequencing was performed according to the manufacturer's instructions on the Applied Biosystems protein sequinator. The results are shown in Table 2; ? indicate cycles where no residue could be assigned.

TABLE 2

AMINO ACID SEQUENCES OF PEPTIDES DERIVED FROM ENDOPROTEINASE DIGESTION OF THE "e" PROTEIN

| | |
|---|---|
| ELys#1 | A-R-L-D-A-V-Q-A-W-D-G-K |
| ELys#2 | R-L-G-F-N-G-V-E-E-S-A-F-Y-L-K |
| ELys#4a | T-F-I-M-L-P-N-A-N-Y-G-G-W-E-G-G-L-A-E-G-Y-F-K |
| Elys#4b | A-V-V-A-D-L-D-E-T-M-L-D-N-?-P-Y-?-?-W-Q-V-?-N-?-?-?-F-D-G-K |
| ELys#5 | S-E-E-H-A-N-M-Q-L-Q-Q-Q-A-V-L-G-L-N-W-M-Q-D-S-G |
| EArg#1 | D-T-Q-G-Q-I-K-A-R-L-D-A-V-Q-A-W-D-G-K |
| EV8(1)#3 | G-Y-F-K-K-D-T-Q-G-Q-I-K-A-R-L-D-A-V-Q-A-W-D-G-K |
| EV8#7 | H-A-N-M-Q-L-Q-Q-Q-A-V-L-G-L-N-W-M-Q-D-S-G-E-Y-K-A-L-A-Y-Q-A-Y-N-A-A-K-V-A-F-D-H-A-K-V-A-K-G-K-K-K-A-V-V-A-D-L-D-E-?-N-?-P-Y-?-G-? |
| EV8#9 | S-A-F-Y-L-K-K-D-K-S-A-K-A-A-R-F-A-E-I-E-K-Q-G-Y-E-I-V-L-Y-V-G-D-N-L-D-D-F-G-N-T-V-Y-G-K-L-N-A-D-R-R-A-F-V-D-Q-N-Q-G-K-F-G-K-T-F-I-M-L-P-? |

Western blot analysis of globomycin-treated recombinant *E. coli* expressing protein "e" revealed the presence of two "e" reactive bands. Globomycin inhibits the action of signal peptidase II which cleaves signal peptides having bacterial lipidation signals. Thus, the protein "e" behaves as expected of a lipoprotein.

II. Preparation of Anti-protein "e" Antibodies

Preparation of Polyclonal Anti-protein "e" Antiserum

Substantially pure protein "e" was used as an immunogen to prepare anti-protein "e" antibodies. The protein "e" was isolated as described above and was mixed with incomplete Freund's adjuvant and emulsified. Rabbits were injected intramuscularly with approximately 50 μg of protein "e" in the adjuvant mixture. Animals were reimmunized approximately 4 weeks and 8 weeks after the initial immunization and bled one week following the final immunization.

Production of Anti-protein "e" Monoclonal Antibodies

Hybridoma cell lines secreting antibodies to protein "e" were obtained by fusion of mouse myeloma cell line P3XAg.653 with spleen cells from a Balb/c mouse immunized against protein "e" as follows. Mice were immunized intraperitoneally at 8 weeks of age with approximately 10 μg of protein "e" enriched OMPs (see above) emulsified in incomplete Freund's adjuvant. Two weeks later, mice were boosted with the identical vaccine preparation. Mice were boosted again on week 5 with 1 μg of the protein "e" enriched outer membrane proteins (OMPs) in saline injected intravenously. Three days after the last immunization, the mice were sacrificed and spleen cells isolated for fusion. Culture supernatants from fused cells were screened for activity against the protein "e" enriched OMP preparation by ELISA. Positive cultures were then screened for activity against total OMPs of Haemophilus by Western blot. Cultures reactive with a band of approximately 28,000 daltons were cloned by limiting dilution. The resulting clones were rescreened for positive secretion against purified protein "e" Cell lines were tested for activity against *E. coli* OMPs and against lipooligosaccharide (LOS) of *H. influenzae* by Western blot. Cell lines which were positive for the protein "e" and negative against both *E. coli* OMPs and Haemophilus LOS were saved.

Binding specificities of monoclonal antibodies from three selected secreting cell lines were determined by competitive radioimmunoassay. Monoclonal antibodies were intrinsically labeled with $^3$H by addition of $^3$H-leucine to growth media. Labeled antibodies were used in solid phase radioimmunoassay in competition with unlabeled antibodies for binding to protein "e". Monoclonal antibody EPR 5.2.1 did not compete with the other two antibodies and recognizes a distinct epitope. Monoclonals EPR 17.1 and EPR 35.24 show some competition with each other, but do not completely block each others binding. Thus, these two antibodies recognize epitopes, which either overlap or have some steric hindrance when bound to protein "e".

III. Reactivity of Anti-protein "e" Antibodies Against Clinical Nontypable *H. Influenza* Isolates Monoclonal and polyclonal anti-protein "e" antibodies were tested against whole cell isolates of clinical nontypable strains. Clinical strains were grown overnight in BHI-XV and aliquots of each culture were seen on SDS-PAGE gels and their reactivity with anti-protein "e" antibodies examined by immunoblot analysis. The results of immunoblot analysis with polyclonal anti-protein "e" antiserum indicated that protein "e" is recognized by the anti-protein "e" antiserum in every strain.

The results of immunoblot analysis of clinical isolates with monoclonal antibodies, Mab EPR-5.2.1 and Mab EPR-17.2.1, are shown in FIGS. 2a and 2b, respectively. Each monoclonal antibody recognizes a different epitope on protein "e". All of the monoclonals react with protein "e" in each clinical isolate. Thus, epitopes on protein "e" are conserved among a variety of clinical nontypable isolates.

IV. General Procedures Used for Preparation of Recombinant Plasmids

Conditions for Restriction Enzyme Digestions

Restriction endonucleases were purchased from BRL (Bethesda, Md.) IBI (New Haven, Conn.), New England Biolabs (Beverly, Mass.) or US Biochemical (Cleveland, Ohio).

Restriction enzyme digestions were carried out by suspending DNA in the appropriate restriction buffer, adding restriction endonuclease and incubating for an appropriate period of time to ensure complete digestion. One unit of enzyme is defined as the amount required to completely digest 1.0 μg of phage lambda DNA in 1 hour in a total reaction mixture of 20 μl volume. Buffers used with the various enzymes are listed below:

Low salt buffer used for ClaI, HpaI, and KpnI digestions consisted of: 10 mM Tris (pH 8.0), 10 mM $MgCl_2$ and 10 mM dithiothreitol (DTT).

Medium salt buffer used for AvaI, EcoRV, HaeII, HincII, HindIII, PstI, SphI, SspI, and XhoI digestions consisted of: 50 mM Tris (pH 8.0), 10 mM $MgCl_2$, 50 mM NaCl, and 10 mM DTT.

High salt buffer us ed for BamHI, EcoRI, PvuI, SalI and XbaI digestions consisted of: 50 mM Tris (pH 8.0), 10 mM $MgCl_2$, 150 mM NaCl and 10 mM DTT.

The buffer used for SmaI digestions consisted of: 10 mM Tris (pH 8.0), 20 mM KCl, 10 mM $MgCl_2$, and mM DTT. All restriction digestions were carried out at 37° C. except TaqI which was carried out at 60° C. and SmaI which was carried out at 25° C.

Gel Purification of DNA Fragments

After restriction enzyme digestions, DNA fragments of varying sizes were separated and purified using gel electrophoreses in low melting temperature agarose (FMC LGT agarose) using 50 mM Tris-acetate 1 mM EDTA buffer pH 7.8 at 10 volts/cm. Agarose concentrations varied from 0.8% to 1.5% depending on the size of fragments to be recovered. DNA bands were visualized by ethidium bromide fluorescence and cut out of the gel. DNA was recovered by melting the agarose at 65° C., adding 4 volumes of 0.65M NaCl, 10M Tris (pH 8.0), 1 mM EDTA to bring the mixture to a final concentration of 0.5.M NaCl, loading the DNA onto a NAGS column (BRL, Bethesda, Md.) equilibrated with 0.5 mM NaCl, 10 mM Tris pH 8.0, 1 mM EDTA (loading buffer), washing the column with 3–5 volumes of loading buffer, and eluting with 2–3 volumes 2 m NaCl, 10 mM Tris pH 8.0, 1 mM EDTA. The DNA eluate was diluted 1:1 with double distilled $H_2O$ and precipitated with 3 volumes of ethanol pellet was washed with 70% ethanol, vacuum dried, and resuspended in 10 mM Tris-HCL buffer, pH 7.5 containing 1 mM EDTA (TE buffer).

DNA Ligation

All ligations were accomplished using T4 DNA ligase. T4 DNA ligase was purchased from BRL (Bethesda, Md.), United States Biochemic is (Cleveland, Ohio) or Boehringer (Indianapolis, Ind.). On unit (U) of T4 DNA ligase is defined as the amount required to yield 50% ligation of HindIII fragments of bacteriophage lambda DNA in 30 minutes at 16° C. in 20 µl volume ligase buffer at a 5'-DNA termini concentration of 0.12 µM (300 µg/ml). DNA ligations were performed in ligase buffer consisting of: 50 mM Tris (pH 7.5), 10 mM $MgCl_2$, 10 mM DTT, 1 mM adenosine triphosphate). Normally a DNA concentration ranging from 2–30 µg/ml, and a molar ratio of vector to insert of 1:2 was used. T4 DNA ligase was added at a ratio of 1 U per 20 µl reaction volume.

Incubations were carried out for 18–24 hours. Temperatures used were 15° C. for cohesive end ligations, and 22° C. for blunt end ligations. If sufficient material was available, ligations were checked by analyzing a portion of the reaction mixture by agarose gel electrophoresis.

Protein Immunoblot Analysis (Western Blot)

Proteins were fixed to nitrocellulose sheets for immunoblot analysis by various techniques, depending on the particular application. Phage plaques were transferred from agar plates by gently placing a sterile 8.1 cm diameter nitrocellulose disc onto the surface of a 10 cm diameter phage titer plate. The sheet was allowed to wet completely, position were marked by punching through the filter with a sterile needle, and the filter was lifted after two minutes.

Colony blots were performed by transferring bacterial colonies to a nitrocellulose sheet, allowing the colonies to grow by lacing the sheet (colony side up) on nutrient agar for 4 to 6 hours, and exposing the sheet to chloroform vapor for 30 minutes to lyse the colonies.

Protein gel transfers were performed by placing an SDS-PAGE gel containing the protein mixture to be analyzed on a nitrocellulose sheet and applying horizontal electrophoresis i a Hoeffer Transphor apparatus at 0.5 A for 14 hours in 25 mM Tris 0.38M glycine pH 8.8 buffer.

Once protein transfer was complete, filters were soaked in 50 mM Tris (pH 8.0), 150 mM NACl, 5% nonfat dry milk (BLOTTO) at 37° C. for one hour in all cases, except colony blots. When colony blots were performed, the filters were soaked overnight at 4° C. in BLOTTO containing 1 mg/ml lysozyme to digest cell debris. Filters were then absorbed with a first antibody probe at an appropriate dilution (determined by trial and error) in BLOTTO for 3 hours at 37° C., washed three times for 15 minutes with BLOTTO, absorbed with horseradish peroxidase conjugated second antibody (Kirkegaard and Perry, Gaithersburg, Md.) at a dilution of 1:500 in BLOTTO for one hour at 37° C. and washed with LOTTO three times for 15 minutes. Filters were placed in 50 mM Tris (pH 7.0), 150 mM NaCl, 0.01% hydrogen peroxide; and 0.06% 4-Chloro-1naphthol (Sigma Chemical Co., St. Louis, Mo.) in methanol was added. If no blue color developed within 20 minutes, the reaction was considered negative. The reaction was stopped by transferring the filter to distilled water and blotting dry.

Dry Filter Hybridization Analysis (Southern Blot)

DNA filter hybridization analysis was carried out according to the method of Smith and Summers (*Anal. Biochem.*, 109:123–129 (1980)). DNA to be analyzed was digested with the appropriate restriction endonuclease(s) and separated by agarose gel electrophoresis in 0.7% agarose (SeaKem, FMC, Rockland, Me.) using 89 mM Tris, 89 mM borate, 8 mM EDTA buffer at 1.5 V/cm. DNA in the gel was depurinated by treatment with 0.25 m HCl for 15 minutes and then denatured in 0.5M NaOH, 1.5M NaCl for a total of 30 minutes. The gel was neutralized with 1M ammonium acetate, 0.02M NaOH for 1 hour and the DNA transferred bidirectionally to nitrocellulose (BA85, Schleicher and Scheull, Keene, N.H.) in the above buffer by paper blotting. After the transfer was complete, approximately 1 hour, the filters were removed, lanes marked with ink, and rinsed in 2X SSC (prepared by dilution from a 20X stock solution containing 175.6 g NaCl and 88.2 g Na citrate per liter) and air dried. DNA fragments were fixed to filters by baking at 80° C. for 2 hours under vacuum.

Probes for DNA hybridization were prepared using a nonradioactive DNA labeling and detection kit purchased from Boehringer-Mannheim (Indianapolis, Ind.). Probe DNA was linearized with an appropriate restriction endonuclease, extracted with a 1:1 mixture of phenol:chloroform, and recipitated with ethanol. The DNA precipitate was dissolved in 10 µl of 10 mM Tris, 1 mM EDTA, pH 8.0 (TE) and denatured by heating to 95° C. for 10 minutes. DNA was quickly cooled in dry ice/ethanol and transferred to ice. The DNA was labeled using the random hexanucleotide mix supplied with the kit as primer, the labeling mixture provided which includes digoxigenin-dUTP (dig-dUTP), and the Klenow fragment of E. coli polymerase I. After the reaction mixture was incubated for 18 hours at 37° C., the reaction was stopped by addition of 1 µl of 0.5M EDTA, pH 8.0. Twenty µg of yeast tRNA was added as carrier and the DNA precipitated with ethanol. Three µg of template DNA yielded approximately 0.5 µg of labeled DNA.

Filters to be probed were rehydrated in deionized water, and incubated at 68° C. in a solution containing 5X SSC, 0.5% blocking reagent (supplied in the kit), 0.1% N-lauryl-sarcosine, 0.02% SDS for 6 hours. The hybridization solution consisted of the above buffer with 30 ng of labeled probe DNA per ml at a ratio of 2.5 ml per 100 cm$^2$ of filter. The probe solution was denatured by heating to 95° C. for 10 minutes and added to the filters. Hybridizations were done at 68° C. for 18 hours. Filters were washed 1X in 2X SS , 0.1% SDS at room temperatures, and 2X 15 minutes in 0.1 X SSC, 0.1 SDS at 68° C. After air drying, hybridized dig-dUTP containing probe was detected using the supplied alkaline phosphatase conjugated anti-digoxigenin tisera at a 1:5000 dilution and development of the alka ine phosphatase- nitroblue tetrazolium-5-bromo-4-chloro-3-indoyl phosphate color reaction for 2–4 hours. The reaction was stopped by rinsing the filter in TE. Under the above conditions, DNA homologies of greater than 98% would show positive binding of the labeled probe.

V. Isolation of protein "e" Gene

The amplified phage library prepared as described in section 6.5.1 was diluted to $10^{-3}$ PFU per ml in TMG and 100 µl of E. coli KH802 (5×10$^9$ cells/ml) were added. After incubation at 37° C. for 20 minutes, 3 ml of LB media containing 10 mM MgCl$_2$ and 0.85% agar at 56° C. were added and the suspension plated onto LB agar plates containing 10 mM MgCl$_2$. Plates were incubated overnight at 37° C. to allow plaque formation, and chilled to 4° C. Plaques were transferred to nitrocellulose filters by absorption and the filters were probed with a pool of monoclonal antibodies which react with protein "e" as described above. Several positive plaque were identified in this manner. Positive plaques were picked and the phage allowed to elute into 1 ml of TMG at 4° C. The phage were amplified by growth in E. coli KH802. Clones were verified by screening phage lysates with SDS-PAGE/Western blot techniques using anti-protein "e" monoclonal antibodies as probes. Positive clones expressed a protein of apparent molecular weight 30,000 daltons which reacted with the anti-protein "e" monoclonal antibodies. This protein was not present in control lysates of negative plaques.

One positive plaque designated EP1-1 was chosen for further analysis. This phage isolate was amplified by growth in E. coli KH802 in LB broth containing 10 mM MgCl$_2$ and the phage particles recovered by precipitation with 20% polyethylene glycol 6000 and banding in CsCl step gradient (See Maniatis et al., supra). Phage DNA was isolated by treatment with 0.1% SDS proteinase K (10 µg/ml, Sigma Chemical Co., St. Louis, Mo.) at 65° C. for 2 h followed by extraction with an equal volume of phenol, then an equal volume of chloroform. The DNA was precipitated by addition of ammonium acetate to 2M and 2.5 volumes of ice-cold ethanol. After incubation at −20° C., the DNA was pelleted by centrifugation at 13,000 x g.

Phage DNA was digested with EcoRI to separate insert fragments from the λ arms. When digested DNA was electrophoresed on a 0.6% agarose gel, a single band of approximately 15 Kb was observed in addition to the λ arms.

Figure 3:
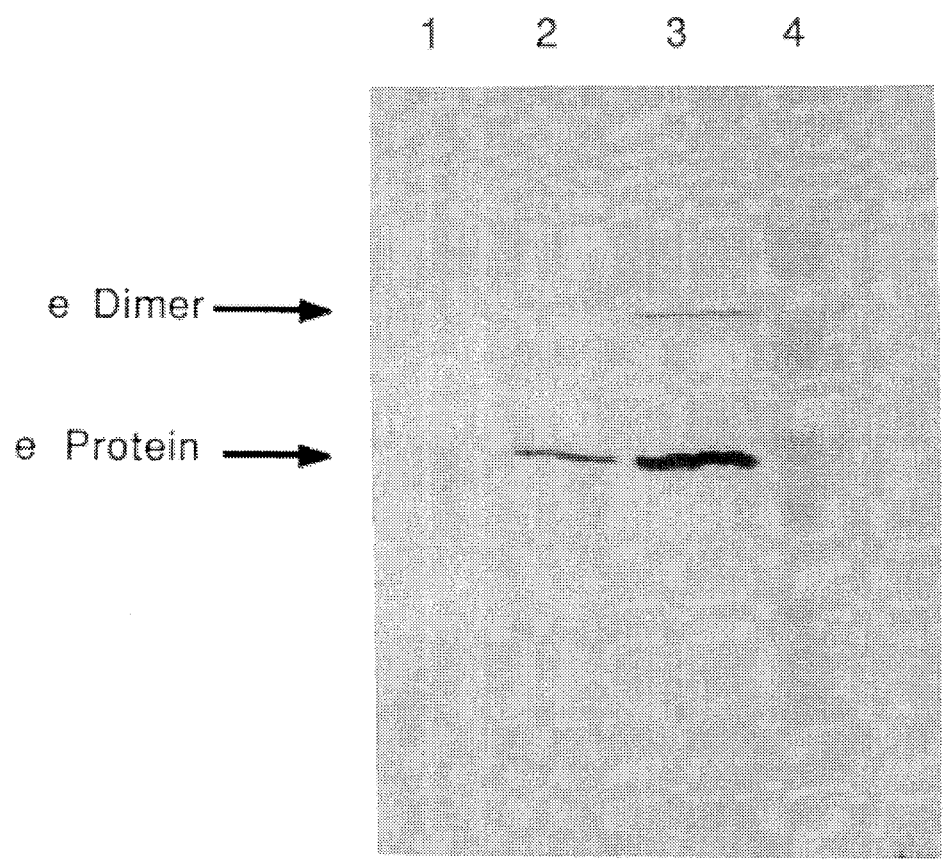
FIG. 3 shows reactivity of anti-e monoclonal antibodies vs. *E. coli* HB101(pPX504).
Figure 4:
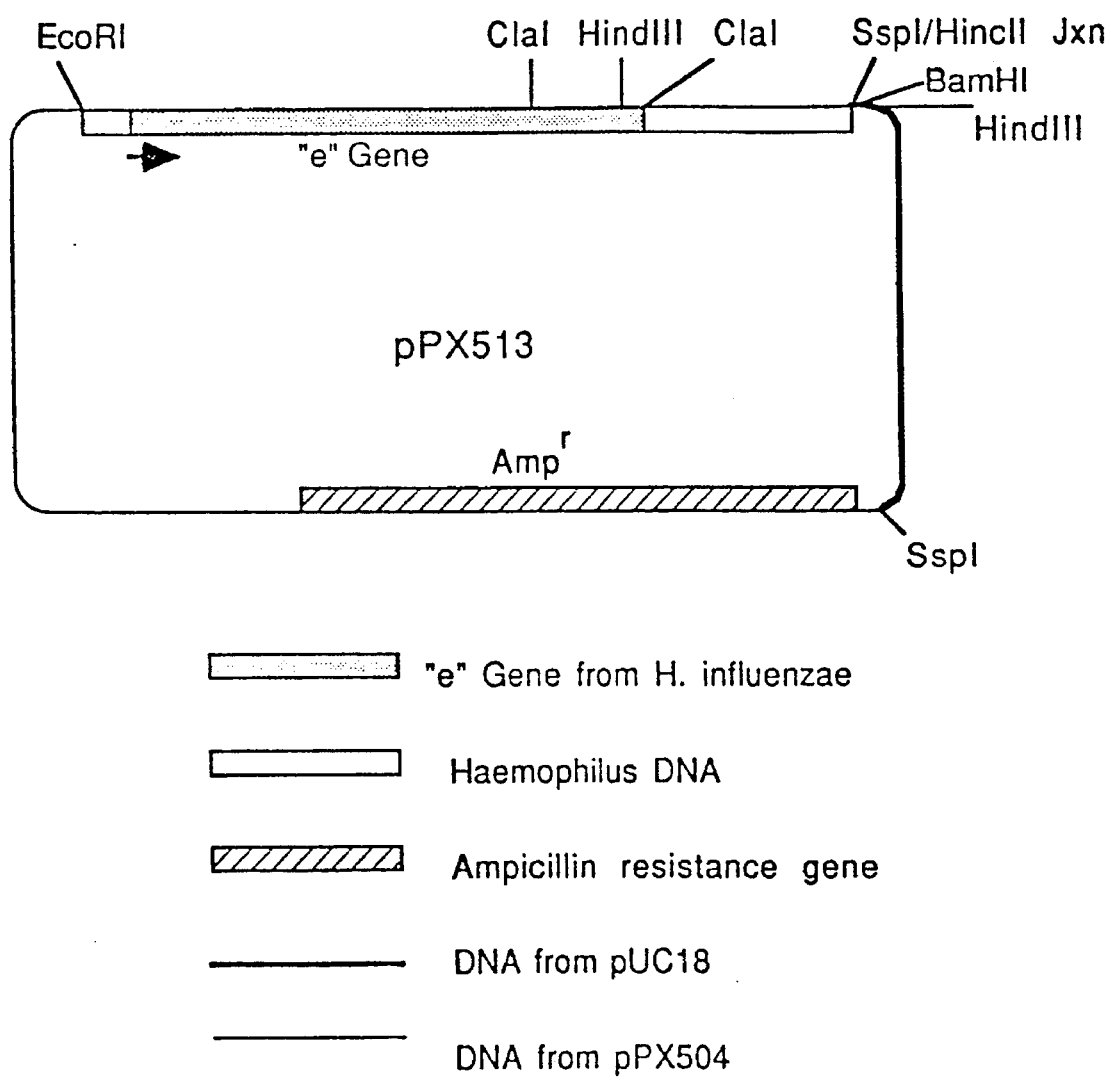
FIG. 4 is a map of plasmid pPX513.
Figure 5:
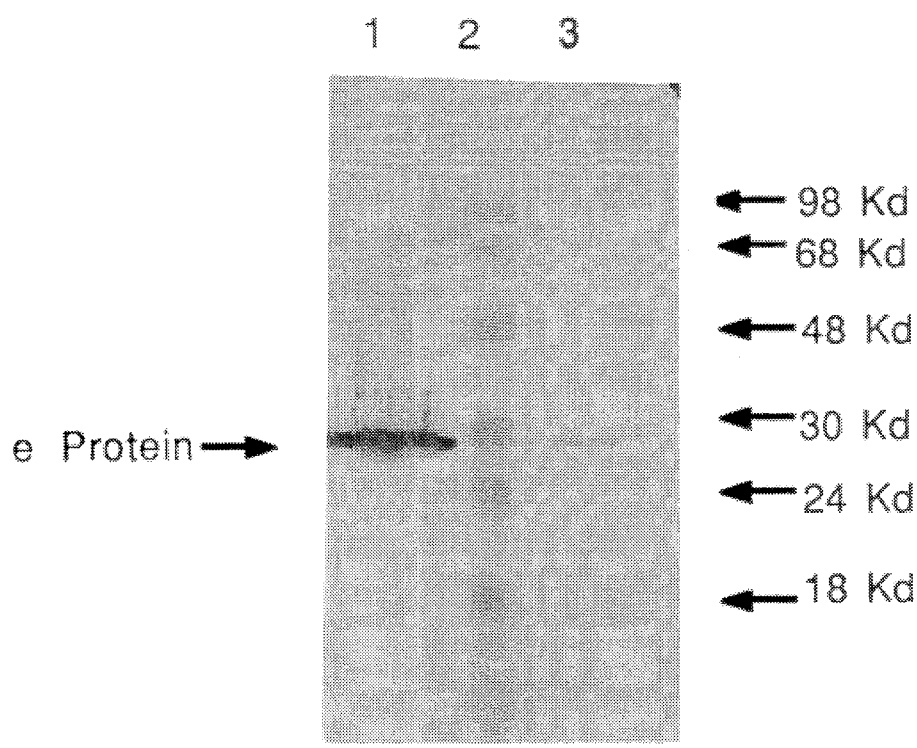
FIG. 5 shows reactivity of anti-e monoclonal antibodies vs. HB101(pPX513).

This 15 Kb fragment was subcloned into the EcoRI site of pUG18. The resulting clones expressed a protein reactive with the anti-protein "e" monoclonal antibodies and of identical molecular size with the native protein "e" as determined by SDS-PAGE/Western blot analysis (FIG. 3). The 15 Kb insert fragment in this plasmid, pPX504, was digested with SspI to delete excess DNA and ligated with SspI-HincII fragment of pUG18. The resulting plasmid, pPX513 (FIG. 4) contained an EcoRI-SspI/HincII insert fragment of approximately 1.6 Kb and expressed a protein which reacted with monoclonal antibodies against protein "e" under regulation of the native Haemophilus promoter (FIG. 5).

VII. Determination of the Nucleotide Sequence of protein "e" Gene

The nucleotide sequence of the protein "e" gene of pPX513 was determined directly from the plasmid by dideoxynucleotide sequencing using the double stranded plasmid as template (Zagursky et al., Tabor et al., supra). M13, M18 and M19 clones of the EcoRI-SspI fragment of pPX513 were sequenced. All sequencing primers were made at Praxis Biologics, Rochester, N.Y. on an Applied Biosystems 380B DNA synthesizer. The primers were made on a 0.2 µmole controlled pore glass column with beta-cyanoethyl phosphate protecting group chemistry. The yield of oligonucleotide was sufficiently pure to allow the use of the primers directly from the column without further purification. The entire sequence of the gene is shown in FIGS. 6A–6B. This ORF encodes a polypeptide of 274 amino acids. The deduced amino acid sequence of protein "e" is shown in FIGS. 7A–7B. The amino acid composition of the deduced protein "e" closely matches that of purified protein "e" (Table 2). The protein "e" gene also has an internal peptide sequence (AA) which aligns with the sequence of peptide L5. The amino terminal residue peptide resembles a membrane transport signal sequence determined for other proteins (Watson, 1984, supra). Thus we conclude that this gene encodes the protein "e".

Figure 8:
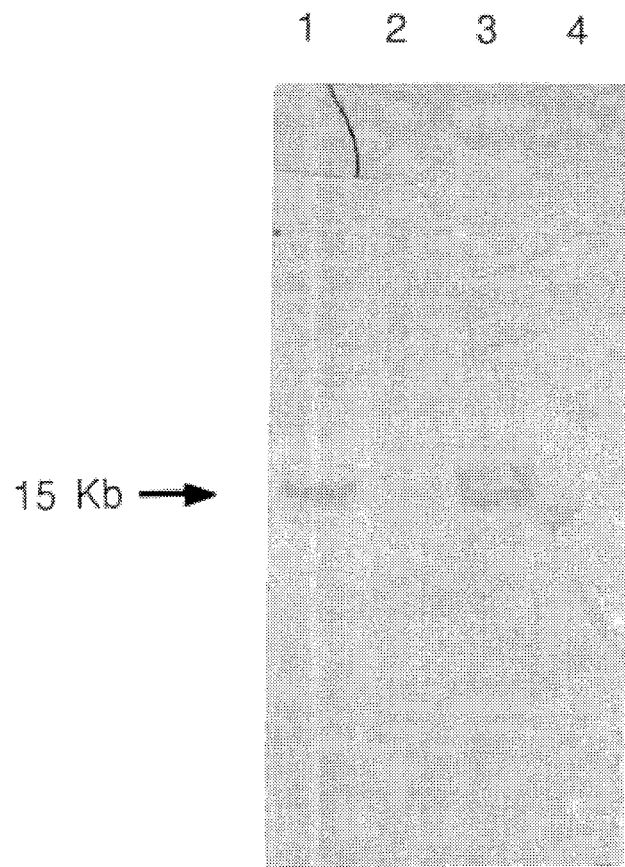
FIG. 8 shows the hybridization of pPX504 to Haemophilus chromosomal DNA.

Chromosomal DNA was prepared from E. coli and H. influenzae strains HDG-85 and Eagan by the method of Marmur (J. Mol. Biol. 3:208–218 (1962)). The DNA was cut with EcoRI and Southern blots prepared as above. These blots were probed with a dig-dUTP labeled protein "e" gene clone prepared s described above. Results are shown in FIG. 8. The probe recognized a single band of approximately 15 Kb in each H. influenzae chromosome and did hybridize to either the lambda standards or the E. coli chromosome showing that the cloned gene is a Haemophilus gene and that it is carried in a single copy.

VIII. Bactericidal Activity of Protein "e" Subunit Vaccine

Anti-protein "e" polyclonal antisera, prepared as described, were examine for their ability to kill Hi in an in vitro complement mediated bactericidal assay system (see Musher et al, Infect. Immun., 39:297–304 (1983); Anderson et al., J. Clin. Invest., 51:31–38 (1972)). Bactericidal assays were performed using precolostral calf serum (PCCS), stored at −70° C., as complement source. The PCCS was prepared for use in the bactericidal (BC) assay by adsorption with whole cells of the nontypable H. influenzae strain being tested. A one milliliter aliquot of an overnight culture grown in BHI-XV was pelleted by centrifugation in an Ependorf table top centrifuge. The pellets were washed by resuspending in sterile phosphate buffered saline containing 0.15 mM CaCl$_2$ and 0.5 mM MgCl$_2$ (PCM) and repeating the centrifugation. One milliliter of PCCS was thawed and used to resuspend the bacterial pellet. The sample was held on ice for one hour. The bacteria were removed by centrifugation, and a second bacterial pellet was resuspended in the PCCS. This was held on ice for one hour. The sample was centrifuged to remove the bacteria an then filter sterilized with a 0.22 micron membrane. The prepared PCCS was held on ice until used. Bacteria were prepared by diluting overnight cultures 1:15 in BHI-XV broth and by incubating at 37° C. with aeration. Cells were grown to an optical density of 0.9 at 490 nm (approximately $10^9$ CFU/ml). Bacteria were diluted 40,000 fold in sterile PCM with 0.5% bovine serum albumin (PCMA). The final dilution contained 25% PCCS (v/v). Immunoglobulins from polyclonal mouse antiprotein "e" antiserum were precipitated with saturated ammonium sulfate at 35% final concentration at 4° C. overnight. The precipitate was collected by centrifugation for 10 minutes at 4° C. in an Eppendorf centrifuge. The supernatant was discarded and the pellet resuspended in PCM at 10 times original volume. The sample was restored to original volume using a Centricon microconcentrator unit with a 10,000 molecular weight cut off membrane. The sample was washed in PCM an additional four times as described above to remove residual ammonium sulfate. Polyclonal rabbit sera were not pretreated for use in the BC assay.

Fifteen microliter of the serum sample were placed in the first well of a sterile 96 well U-bottom microtiter plate held on ice. Two-fold serial dilutions using PCMA were done in the remaining wells. The plates were removed from the ice an 15 µl of the cell/complement mixture were added to the serum in the wells. The plates were incubated at 37° C. or 45 minutes. A 10 µl sample was asceptically remove from each well and spread on a BHI-XV plate. The plates were incubated overnight at 37° C. The bactericidal titer was determined as the reciprocal of the highest dilution of serum capable of reducing the number of CFUs resuspended in PCMA at 10 times original volume. The sample was restored to original volume using a Centricon microconcentrator unit with a 10,000 molecular weight cut off membrane. The sample was washed in PCM an additional four times as described above to remove residual ammonium sulfate. Polyclonal rabbit sera was not pretreated for use in the BC assay.

Fifteen microliters of the serum sample were placed in the first well of a sterile 96 well U-bottom microtiter plate held on ice. Two-fold serial dilutions using PCMA were done in the retaining wells. The plates were removed from the ice and 15 µl of the cell/complement mixture were added to the serum in the wells. The plates were incubated at 37° C. for 45 minutes. A 10 µl sample was asceptically removed from each well and spread on a BHI-XV plate. The plate were incubated overnight at 37 C. The bactericidal titer was determined as the reciprocal of the highest dilution of serum capable of reducing the number of CFUs by 50% compared to a non-antibody containing control well.

Results from one such experiment are shown below;

TABLE 3

Bactericidal Activity of Rabbit Anti-protein "e" Antiserum Against Non-Typable *H. Influenzae* Clinical Isolates

| Time | Strain | Anti-protein "e" Titer* |
|---|---|---|
| WEEK 0 | N90 | 5 |
| WEEK 6 | N90 | 160 |
| WEEK 0 | S2 | 10 |
| WEEK 6 | S2 | >640 |
| WEEK 0 | 0246E | 5 |

TABLE 3-continued

Bactericidal Activity of Rabbit Anti-protein "e" Antiserum Against Non-Typable *H. Influenzae* Clinical Isolates

| Time | Strain | Anti-protein "e" Titer* |
|---|---|---|
| WEEK 6 | 0246E | 40 |
| WEEK 0 | HST34 | 5 |
| WEEK 6 | HST34 | 20 |

*Reciprocal highest dilution capable of killing 50% or more of the NTHi in the assay.

As can be seen from Table 3, anti-protein "e" antibody has BC activity against non-typable *H. influenzae* strains.

The *H. influenzae* OMP designated P4, a protein of about 28,000 daltons molecular weight, has been shown to be non-protective in the passive protection assay in infant rats (Granoff and Munsen, *J. Infect. Dis.* 1986. 153:448–461). All known immunogens of *H. influenzae* that are protective in a passive transfer of antibody assay also elicits bactericidal antibodies. Here we show that the *H. influenzae* protein "e" of about 28,000 daltons to elicit bactericidal antibodies and thus these antibodies would be expected to be protective.

Synergy of Anti-protein "e" with Other Antibodies

Other investigators have reported that antibodies against some OMPs can block the bactericidal activity of antibodies directed against other OMPs. K. A. Joiner, et al. (1985) *J. Clin. Invest.* 76:1765–1772. An assay for BC was performed in order to determine whether antiprotein "e" antibodies have blocking effects when antibodies directed against other Hi components are present. The details of the assay for bactericidal activity of antibody are given above. Bactericidal titers are read as the reciprocal of the highest dilution of an antisera capable of killing >50% of a defined number of bacteria. The assay may be performed with either non-typable *H. influenzae* (NTHi) or type b *H. influenzae*. NTHi show greater serum sensitivity and are thus somewhat easier to kill in the assay, but are more difficult to use. The bactericidal titers are usually shown with the preimmune and immune sera. This is because of the extremely variable sensitivity of NTHi to killing by anti-OMP antibodies. Thus titers may cover a wide range. Showing pre and post immune sera allows us to show the specificity of the killing no matter what the titer.

To determine if anti-protein "e"-antibody has this blocking effect with antibodies against another OMP, we examined the effect of mixing the anti-protein "e" with antibody against a recombinant Haemophilus outer membrane protein, rPCP. The bactericidal titers of the individual antisera and the mixtures tested are shown in table 4. No blocking effects were observed. In contrast, the BC titer of the mixture was always greater than the titer of either of the individual antisera. If there was no additive effect, one could expect that the BC titer of the mixture would be the same as the titer of the more active of the individual antisera. If there was an additive effect, then the titer of the mixture would be expected to be the sum of the titers of the individual antisera. However, the titers of the mixture show synergy where the BC titer of the mixture is greater than the sum of the titers of the individual antisera.

TABLE 4

| Strain | anti-e | | anti-rPCP | | anti e & anti-rPCP | |
|---|---|---|---|---|---|---|
| | Preimmune | Immune | Preimmune | Immune | Preimmune | Immune |
| Hst 33 | <1/5 | 1/10 | 1/10 | 1/20 | 1/5 | >1/32 |
| N0264E | <1/5 | 1/40 | <1/5 | 1/5 | 1/5 | 1/160 |
| N0133E | 1/10 | 1/40 | 1/10 | 1/80 | 1/5 | 1/160 |
| N1955 | 1/5 | 1/40 | <1/5 | 1/20 | 1/5 | >1/640 |

IX. Non-Lipidated Form of Protein "e"

In order to create a non-lipidated version of protein "e", site directed mutagenesis was employed. In the amino terminal end of the "e" sequence, a BamHI site was created by site directed mutagenesis using the dut-ung system supplied by Biorad Laboratories (Richmond, Calif.). The following changes were made in the "e" gene:

Sequence of gene encoding the amino terminus of the mature "e" protein

```
      |  TGT  GGT  TCA  CAC  .....
Sig. seq. |  Cys  Gly  Ser  His
```

Changed to

```
      .....  TGT  GGA  TCC  CAC  .....
             Cys  Gly  Ser  His
```

This was done by cloning the 997 bp EcoRI-DraI fragment containing "e" gene into the EcoRI-SmaI sites of M13mp19. Single stranded DNA was isolated after infection of dut, ung. *E. coli* strain CJ236. This DNA contains uracil residues which replace thymidine residues and is non-infectious for normal *E. coli*. The single stranded U-DNA was mixed with a single stranded primer containing the desired mutations and homologous flanking sequences and the DNAs annealed slowly. The primer was extended on the DNA using all four dNTPs and the Klenow fragment of *E. coli* polymerase to complete the circle. Wild type *E. coli* were infected with the M13 DNA causing only the newly synthesized strand to be replicated and inserting the mutation in the gene. The M13 DNA containing the "e" gene with the BamHI site was isolated, the gene isolated by digestion with BamHI (a BamHI site also exists 3' to the gene from the multiple cloning site region of the M13mp19) and subcloned into pUG8. The resulting clones, designated pPX524, were screened with monoclonal antibodies to protein "e". After screening with monoclonal antibodies to protein "e" for expressing clones, no positive isolates were obtained. Analysis of clones showed that all contained the "e" gene, in the reverse (non-expressing orientation. The signaless "e" gene has been expressed under control of a regulated promotor; to express the gene under lac control, the "e" gene was removed from pPX524 by digestion with HincII and EcoRI and directionally cloned into pUC9 at the EcoRI and SmaI sites yielding a fusion with the following joint sequence in plasmid pPX525:

ATG ACC ATG ATT ACG CCA AGC TTG GCT GCA GGT CGA CGG met thr met ile thr pro ser leu ala ala gly arg arg <------------------ lac α peptide ------------------>

-continued
ATC CCC|GAC GGA TCC CAC CAA ile pro |asp gly ser his gln

----> <---- "e" gene ---->

The fusion is weakly expressed and has been visualized by reactivity to monoclonal antibodies.

The signaless "e" gene has also been fused onto the PCP-PAL fusion by isolating the HincII fragment containing the signales "e" gene from pPX525 and ligating it into StuI-EcoRI digested pPX521 which containes the PCP-PAL fusion. The fusion joint formed is as follows:

TAC GTA GAG GGA CGG ATC CCC|GAC GGA TCC CAC CAA....

tyr val glu ala arg ile pro |asp gly ser his gln

<-- PCP-PAL Fusion protein --> <------ "e" gene ---->

Expression of the triple fusion was confirmed by Western blot of DH5α(F'lacIq) cells containing the triple fusion plasmid with monoclonal antibodies directed against PCP, PAL, and "e" proteins.

Sequences of the fusion joints and the site directed mutagenesis have been confirmed by DNA sequencing.

Deposit of Microorganism

*E. coli* strain JM103 (pPX513) was deposited with the Agricultural Research Culture Collection (NRRL), Peoria, Ill. and has been assigned the accession number NRRL B-18444 deposited on Jan. 26, 1989.

*E. coli* strain DH5α(F'lacIq, pPX525) was deposited with the NRRL on Mar. 8, 1990, and has been assigned Accession Number NRRL B-18629.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A vaccine composition comprising essentially pure protein "e" of *Haemophilus influenzae* or a peptide of protein "e" comprising an epitope or epitopes thereof, in a pharmaceutically acceptable vehicle; wherein the protein "e" of *Haemophilus influenzae* or the peptide of protein "e" elicits a protective immune response in a mammalian host.

2. A vaccine composition of claim 1, further comprising at least one additional antigen of one or more organisms.

3. A vaccine composition of claim 2, wherein the organism is a bacterium, virus, parasite or fungus.

4. A vaccine composition of claim 2, wherein the organism or organisms are etiologic agent(s) of otitis media.

5. A vaccine composition of claim 4, wherein the organism is selected from the group consisting of *Streptococcus pneumoniae, Streptococcus pyogenes,* group A, *Staphylococcus aureus, Branhamella catarrhalis* and respiratory syncytial virus.

6. A vaccine composition of claim 2, wherein the additional antigen is an oligo- or polysaccharide antigen of a bacterium.

7. A vaccine composition of claim 6, wherein the antigen is polyribosylribitolphosphate.

8. A vaccine composition of claim 6, wherein the oligo- or polysaccharide antigen is conjugated to a carrier peptide or protein.

9. A vaccine composition of claim 8, wherein the carrier peptide is tetanus toxin or toxoid, diphtheria toxin or toxoid, Pseudomonas exotoxin A, heat labile toxin of *E. coli,* rotaviral particles and any mutant forms, fragments or antigenic epitopes thereof.

10. A vaccine composition of claim 2, wherein the additional antigen is an outer membrane protein of *Haemophilus influenzae.*

11. A vaccine composition of claim 10, wherein the outer membrane protein is selected from the group consisting of the 15,000-dalton peptidoglycan-associated outer membrane lipoprotein (PAL), the 15,000-dalton Haemophilus lipoprotein PCP, conjugates or fusion proteins of PAL and PCP and segments of PAL or PCP.

12. A vaccine composition comprising an antigen conjugate consisting essentially of protein "e" of *Haemophilus influenzae* or a peptide of protein "e" comprising an epitope or epitopes thereof, conjugated to an antigen of an organism or an epitope or epitopes thereof, in a pharmaceutically acceptable vehicle; wherein the protein "e" of *Haemophilus influenzae* or the peptide of protein "e" elicits a protective immune response in a mammalian host.

13. A vaccine composition of claim 12, wherein the organism is *Haemophilus influenzae.*

14. A vaccine composition of claim 13, wherein the antigen is an oligo- or polysaccharide antigen of *Haemophilus influenzae.*

15. A vaccine composition of claim 14, wherein the antigen is polyribosylribitolphosphate.

16. A vaccine composition of claim 12, wherein the antigen is an outer membrane protein of *Haemophilus influenzae.*

17. A vaccine composition of claim 16, wherein the outer membrane protein is selected from the group consisting of the 15,000-dalton peptidoglycan-associated outer membrane lipoprotein (PAL), the 15,000-dalton Haemophilus lipoprotein PCP, conjugates or fusion proteins of PAL and PCP and segments of PAL or PCP.

18. A vaccine composition comprising an immunogenic amount of essentially pure protein "e" of *Haemophilus influenzae* in a pharmaceutically acceptable vehicle; wherein the protein elicits a protective immune response in a mammalian host.

19. A method of immunizing against *Haemophilus influenzae,* comprising administering to a mammalian host an immunogenic amount of essentially pure protein "e" of *Haemophilus influenzae* or a peptide of protein "e" comprising an epitope or epitopes thereof; wherein the protein "e" of *Haemophilus influenzae* or the peptide of protein "e" elicits a protective immune response in the mammalian host.

20. A method of claim 19, wherein protein "e" of *Haemophilus influenzae* has the amino acid sequence shown in FIG. 7.

21. A method of claim 19, wherein the protein "e" or peptide of protein "e" is administered in the same composition with at least one other antigen of *Haemophilus influenzae.*

22. A method of claim 21, wherein the other antigen is an oligo- or polysaccharide or an outer membrane protein of *Haemophilus influenzae.*

23. A method of claim 22, wherein the polysaccharide is polyribosylribitolphosphate.

24. A method of claim 22, wherein the outer membrane protein is selected from the group consisting of the 15,000-dalton peptidoglycan-associated outer membrane lipoprotein (PAL), the 15,000-dalton Haemophilus lipoprotein PCP, conjugates or fusion proteins of PAL and PCP and segments of PAL or PCP.

25. A method of claim 19, wherein the protein "e" is administered as a conjugate or fusion protein with at least one other antigen of *Haemophilus influenzae* or a carrier protein.

26. A method of immunizing against *Haemophilus influenzae,* comprising administering to a mammalian host an immunogenic amount of essentially pure protein "e" of *Haemophilus influenzae;* wherein the protein elicits a protective immune response in the mammalian host.

27. A method of immunizing against *Haemophilus influenzae* and at least one other organism, comprising administering an immunogenic amount of essentially pure protein "e" of *H. influenzae* or a peptide, of protein "e" comprising an epitope or epitopes thereof, wherein the protein "e" of *Haemophilus influenzae* or the peptide of protein "e" elicits a protective immune response in a mammalian host; and an immunogenic amount of an antigen, epitope or epitopes thereof, of at least one other organism.

28. A vaccine composition of claim 1, further comprising an adjuvant.

29. A vaccine composition of claim 12, further comprising an adjuvant.

30. A vaccine composition of claim 18, further comprising an adjuvant.

31. A vaccine composition of claim 1, which is capable of eliciting bactericidal antibodies.

32. A vaccine composition of claim 1, which is capable of eliciting opsonic antibodies.

33. A vaccine composition of claim 1, which is capable of eliciting bactericidal and opsonic antibodies.

\* \* \* \* \*